(12) United States Patent
Xiong et al.

(10) Patent No.: US 7,892,764 B2
(45) Date of Patent: Feb. 22, 2011

(54) SYSTEM FOR SEIZURE SUPPRESSION

(75) Inventors: Zhigang Xiong, Beaverton, OR (US);
Roger P. Simon, Portland, OR (US)

(73) Assignee: Legacy Emanuel Hospital & Health Center, Portland, OR (US)

( * ) Notice: Subject to any disclaimer, the term of this patent is extended or adjusted under 35 U.S.C. 154(b) by 68 days.

(21) Appl. No.: 11/944,332

(22) Filed: Nov. 21, 2007

(65) Prior Publication Data

US 2008/0242588 A1    Oct. 2, 2008

Related U.S. Application Data

(60) Provisional application No. 60/860,522, filed on Nov. 21, 2006, provisional application No. 60/959,987, filed on Jul. 17, 2007.

(51) Int. Cl.
*G01N 33/566* (2006.01)

(52) U.S. Cl. .................. 435/7.2; 435/7.21; 436/501

(58) Field of Classification Search ........................ None
See application file for complete search history.

(56) References Cited

U.S. PATENT DOCUMENTS

| | | | | |
|---|---|---|---|---|
| 5,800,459 | A | * 9/1998 | Spano et al. | 607/2 |
| 2003/0186860 | A1 | * 10/2003 | Welsh et al. | 514/12 |
| 2009/0291150 | A1 | 11/2009 | Welsh et al. | |

OTHER PUBLICATIONS

Waldmann et al. A Proton-gated Cation Channel Involved in Acid Sensing, Mar. 13, 1997, Nature 386:173-177.*
Ali et al. Evidence of the Antiepileptic Potential of Amiloride with Neuropharmacological Benefits in Rodent Models of Epilepsy and Behavior, Mar. 3, 2004, Epilepsy & Behavior5:322-328.*
McNamara,J.O., Huang,Y.Z. & Leonard,A.S. Molecular signaling mechanisms underlying epileptogenesis. *Sci. STKE.* 2006, re12 (2006).
Pitkanen,A. & Halonen,T. Prevention of epilepsy. *Trends Pharmacol. Sci.* 19, 253-255 (1998).
Meldrum,B.S. & Rogawski,M.A. Molecular targets for antiepileptic drug development. *Neurother.* 4, 18-61 (2007).
Siesjo,B.K., Katsura,K. & Kristian,T. Acidosis-related damage. *Adv. Neurol.* 71, 209-233 (1996).
Simon RP. Status epilepticus mechanisms and management . Wasterlain, C.G & Treiman D.M. (eds.), pp. 149 (The MIT Press,2006).
Chesler,M. & Kaila,K. Modulation of pH by neuronal activity. *Trends. Neurosci* 15, 396-402 (1992).
Siesjo,B.K. & Wieloch,T. Epileptic brain damage: pathophysiology and neurochemical. *Adv. Neurol.* 44:813-47., 813-847 (1986).
Huang,Y. & McNamara,J.O. Ischemic stroke: "acidotoxicity" is a perpetrator. *Cell* 118, 665-666 (2004).
Benveniste,M. & Dingledine,R. Limiting stroke-induced damage by targeting an acid channel. *N. Engl. J. Med.* 352, 85-86 (2005).
Xiong,Z.G. et al. Neuroprotection in ischemia: blocking calcium-permeable Acid-sensing ion channels. *Cell* 118, 687-698 (2004).

Meller,R. et al. Seizure-like activity leads to the release of BAD from 14-3-3 protein and cell death in hippocampal neurons in vitro. *Cell. Death. Differ.* 10, 539-547 (2003).
Furshpan,E.J. & Potter,D.D. Seizure-like activity and cellular damage in rat hippocampal neurons in cell culture. *Neuron.* 3, 199-207 (1989).
Escoubas,P. et al. Isolation of a tarantula toxin specific for a class of proton-gated Na+ channels. *J. Biol. Chem.* 275, 25116-25121 (2000).
Avoli,M. et al. Network and pharmacological mechanisms leading to epileptiform synchronization in the limbic system in vitro. *Prog. Neurobiol.* 68, 167-207 (2002).
Wong,M. & Yamada,K.A. Developmental characteristics of epileptiform activity in immature rat neocortex: a comparison of four in vitro seizure models. *Brain Res. Dev. Brain Res.* 128, 113-120 (2001).
Alvarez,d.I.R. et al. Distribution, subcellular localization and ontogeny of ASIC1 in the mammalian central nervous system. *J. Physiol* 546, 77-87 (2003).
Stasheff,S.F., Bragdon,A.C. & Wilson,W.A. Induction of epileptiform activity in hippocampal slices by trains of electrical stimuli. *Brain Res.* 344, 296-302 (1985).
Araki,T., Simon,R.P., Taki,W., Lan,J.Q. & Henshall,D.C. Characterization of neuronal death induced by focally evoked limbic seizures in the C57BL/6 mouse. *J. Neurosci. Res.* 69, 614-621 (2002).
Pignataro,G., Simon,R.P. & Xiong,Z.G. Prolonged activation of ASIC1a and the time window for neuroprotection in cerebral ischaemia. *Brain.* 130, 151-158 (2007).
Chesler,M. & Chan,C.Y. Stimulus-induced extracellular pH transients in the in vitro turtle cerebellum. *Neuroscience.* 27, 941-948 (1988).
Wemmie,J.A., Price,M.P. & Welsh,M.J. Acid-sensing ion channels: advances, questions and therapeutic opportunities. *Trends Neurosci.* 29, 578-586 (2006).
Miesenbock,G., De Angelis,D.A. & Rothman,J.E. Visualizing secretion and synaptic transmission with pH-sensitive green fluorescent proteins. *Nature.* 394, 192-195 (1998).
Zha,X.M., Wemmie,J.A., Green,S.H. & Welsh,M.J. Acid-sensing ion channel 1a is a postsynaptic proton receptor that affects the density of dendritic spines. *Proc. Natl. Acad. Sci. U. S. A.* 103, 16556-16561 (2006).

(Continued)

*Primary Examiner*—John D Ulm
(74) *Attorney, Agent, or Firm*—Kolisch Hartwell, P.C.

(57) ABSTRACT

Systems, including methods and compositions, for seizure suppression, such as inhibition of epileptic seizures. In some embodiments, the methods may provide a screen for anti-seizure drugs. One or more compositions may be selected based on an ability to affect a response of biological cells to a change in extracellular pH and/or to affect an activity of at least one acid sensing ion channel (ASIC). Based on the one or more compositions selected, at least one drug candidate may be assayed for inhibition of seizure-like electrical activity and/or seizures. In some embodiments, the methods and compositions may, respectively, administer and provide an effective amount of PcTX1, a peptide derivative of PcTX1 amiloride, an amiloride derivative, or a combination thereof to a subject prone to seizures and/or having a seizure, in order to suppress seizure activity.

17 Claims, 23 Drawing Sheets

OTHER PUBLICATIONS

Hesselager,M., Timmermann,D.B. & Ahring,P.K. pH Dependency and desensitization kinetics of heterologously expressed combinations of acid-sensing ion channel subunits. *J. Biol. Chem.* 279, 11006-11015 (2004).

Wang,W.Z. et al. Modulation of acid-sensing ion channel currents, acid-induced increase of intracellular Ca2+, and acidosis-mediated neuronal injury by intracellular pH. *J. Biol. Chem.* 281, 29369-29378 (2006).

DeVries,S.H. Exocytosed protons feedback to suppress the Ca2+ current in mammalian cone photoreceptors. *Neuron.* 32, 1107-1117 (2001).

Krishtal,O.A., Osipchuk,Y.V., Shelest,T.N. & Smirnoff,S.V. Rapid extracellular pH transients related to synaptic transmission in rat hippocampal slices. *Brain Res.* 436, 352-356 (1987).

Chesler,M. Regulation and modulation of pH in the brain. *Physiol Rev.* 83, 1183-1221 (2003).

Urbanics,R., Leniger-Follert,E. & Lubbers,D.W. Time course of changes of extracellular H+ and K+ activities during and after direct electrical stimulation of the brain cortex. *Pflugers Arch.* 378, 47-53 (1978).

Wemmie,J.A. et al. The acid-activated ion channel ASIC contributes to synaptic plasticity, learning, and memory. *Neuron.* 34, 463-477 (2002).

Immke,D.C. & McCleskey,E.W. Lactate enhances the acid-sensing Na+ channel on ischemia-sensing neurons. *Nat. Neurosci* 4, 869-870 (2001).

Steen,K.H., Reeh,P.W., Anton,F. & Handwerker,H.O. Protons selectively induce lasting excitation and sensitization to mechanical stimulation of nociceptors in rat skin, in vitro. *J. Neurosci.* 12, 86-95 (1992).

"Seizure Termination by Acidosis Depends on ASIC1a" by Ziemann et el., vol. 11 No. 7, Jul. 2008, Nature Neuroscience, pp. 816-822.

* cited by examiner

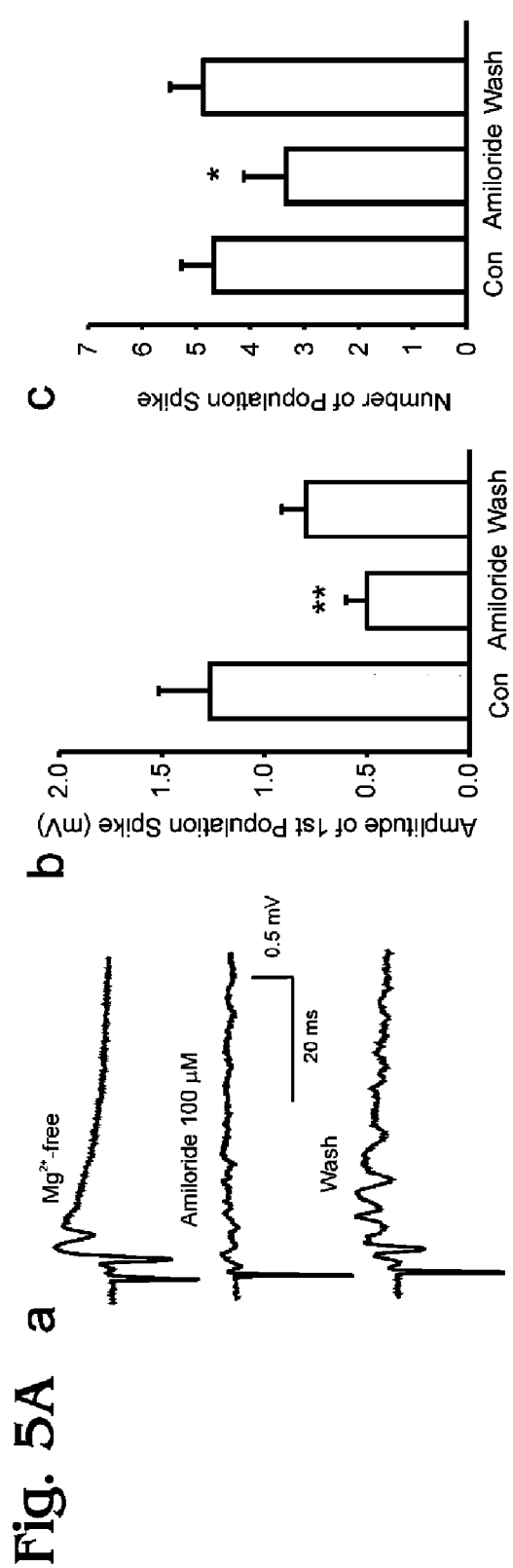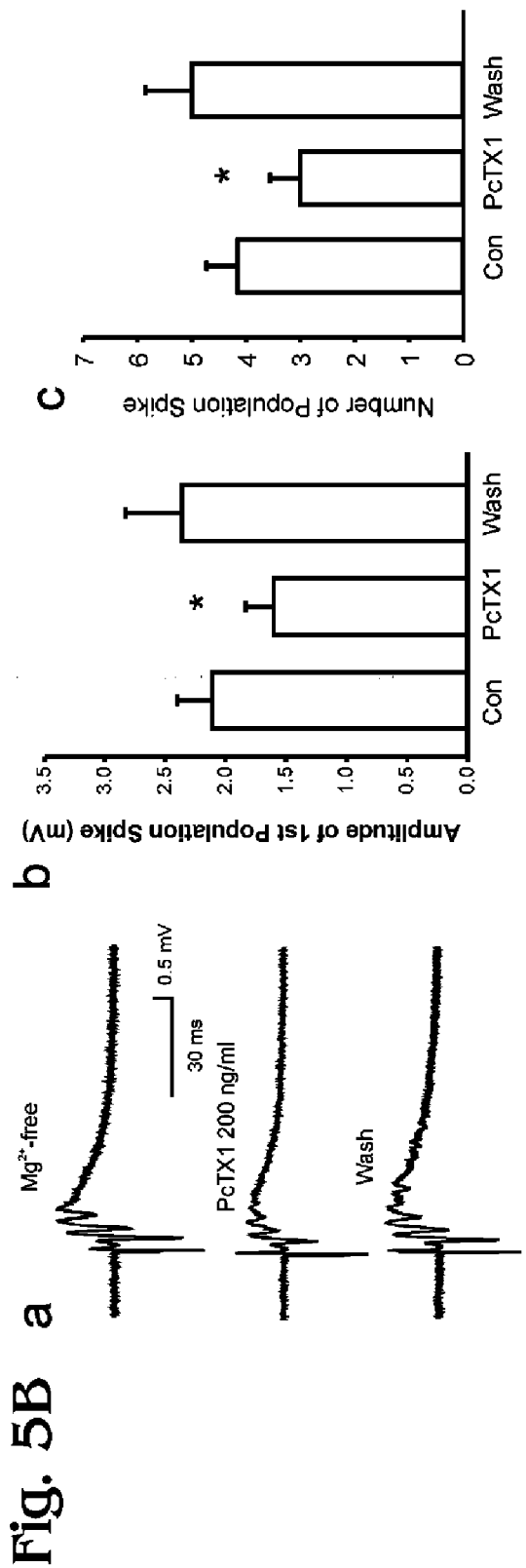
Fig. 5A
Fig. 5B

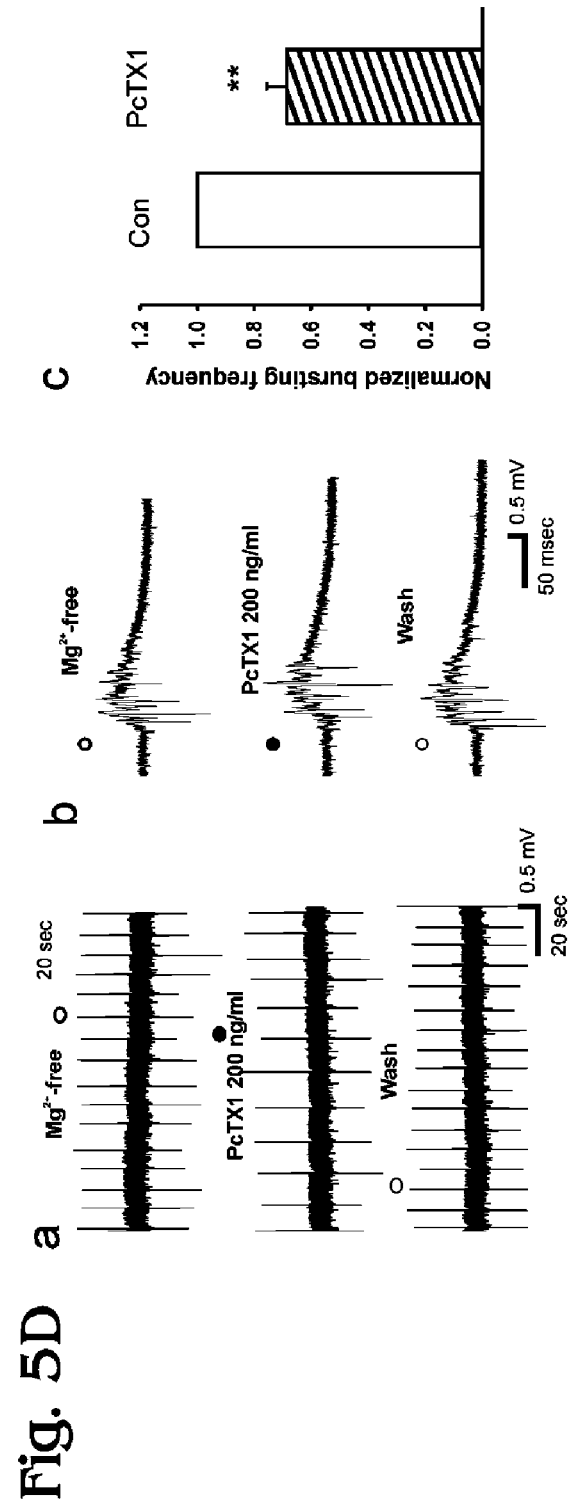
Fig. 5C
Fig. 5D

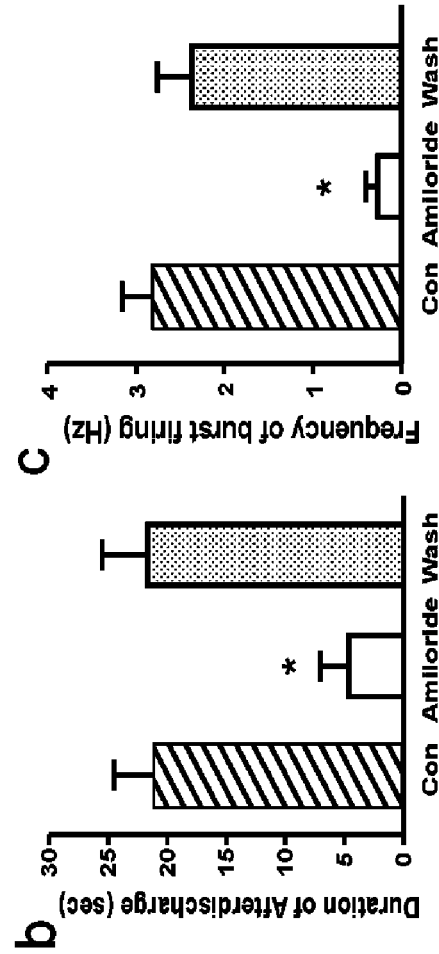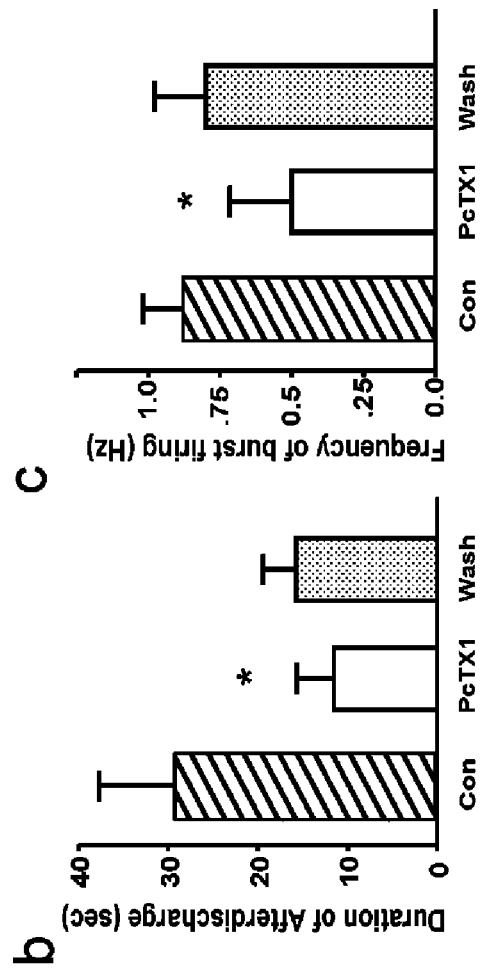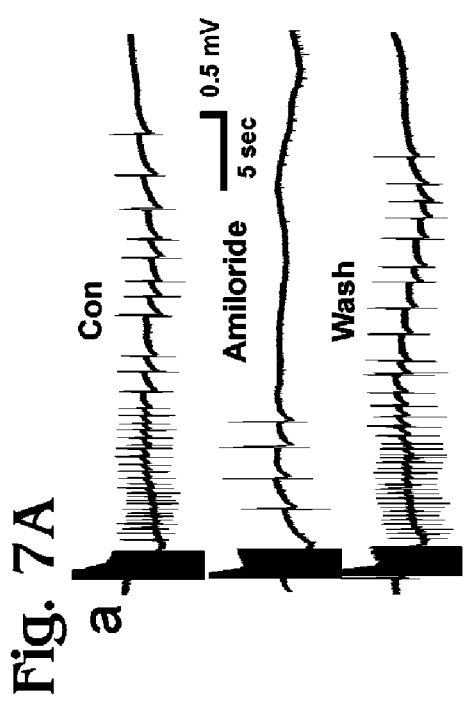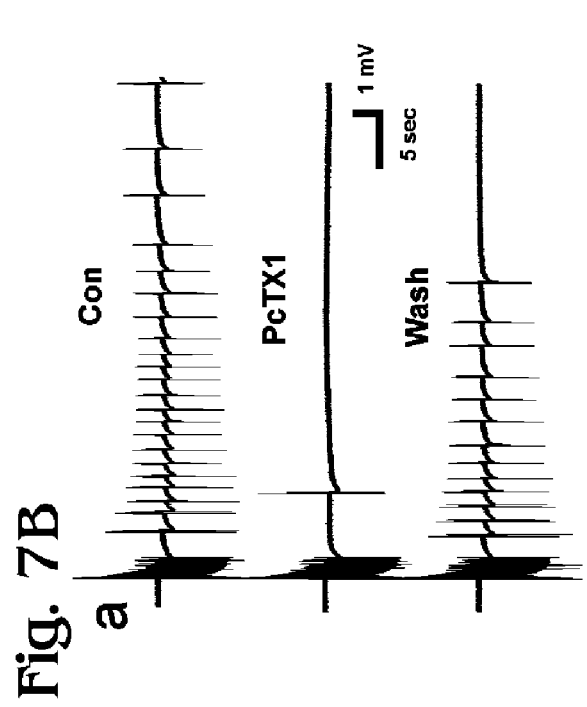
Fig. 7A
Fig. 7B

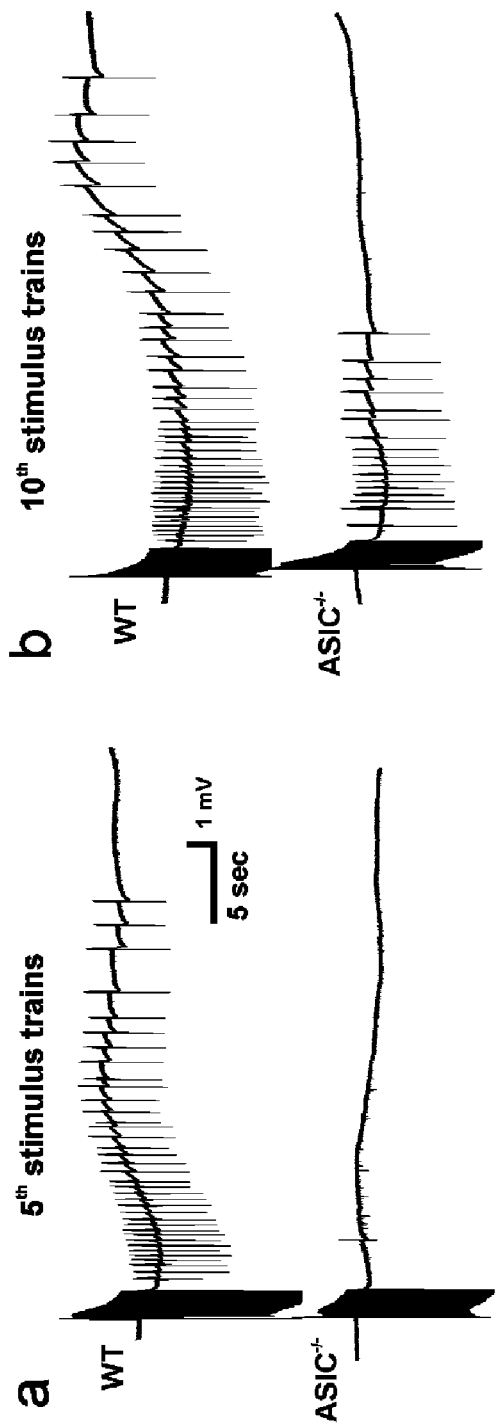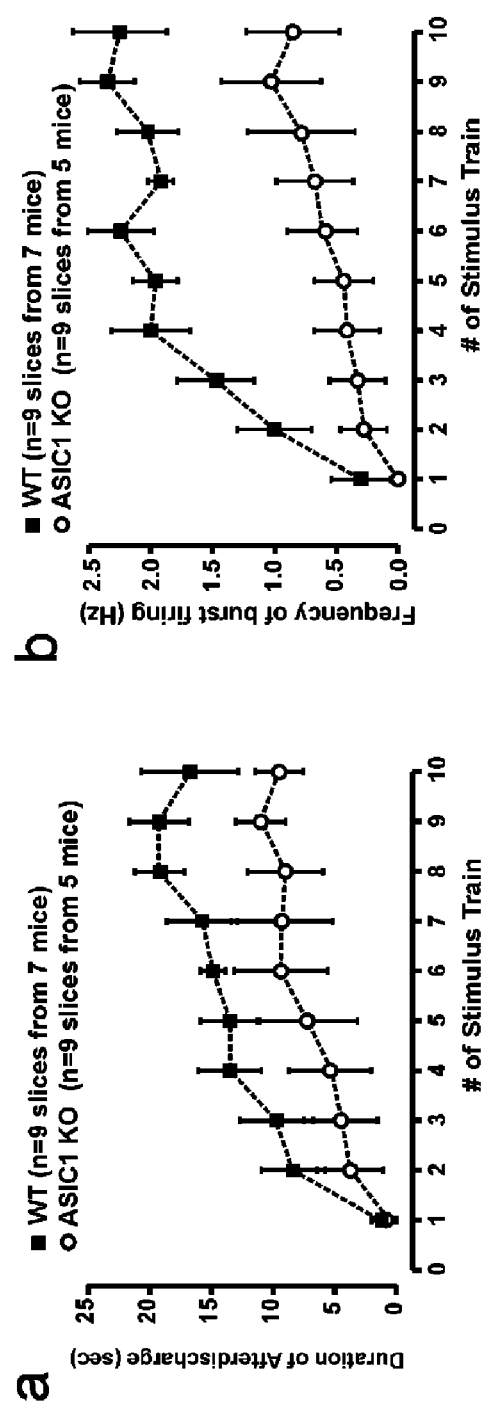
Fig. 7C
Fig. 7D

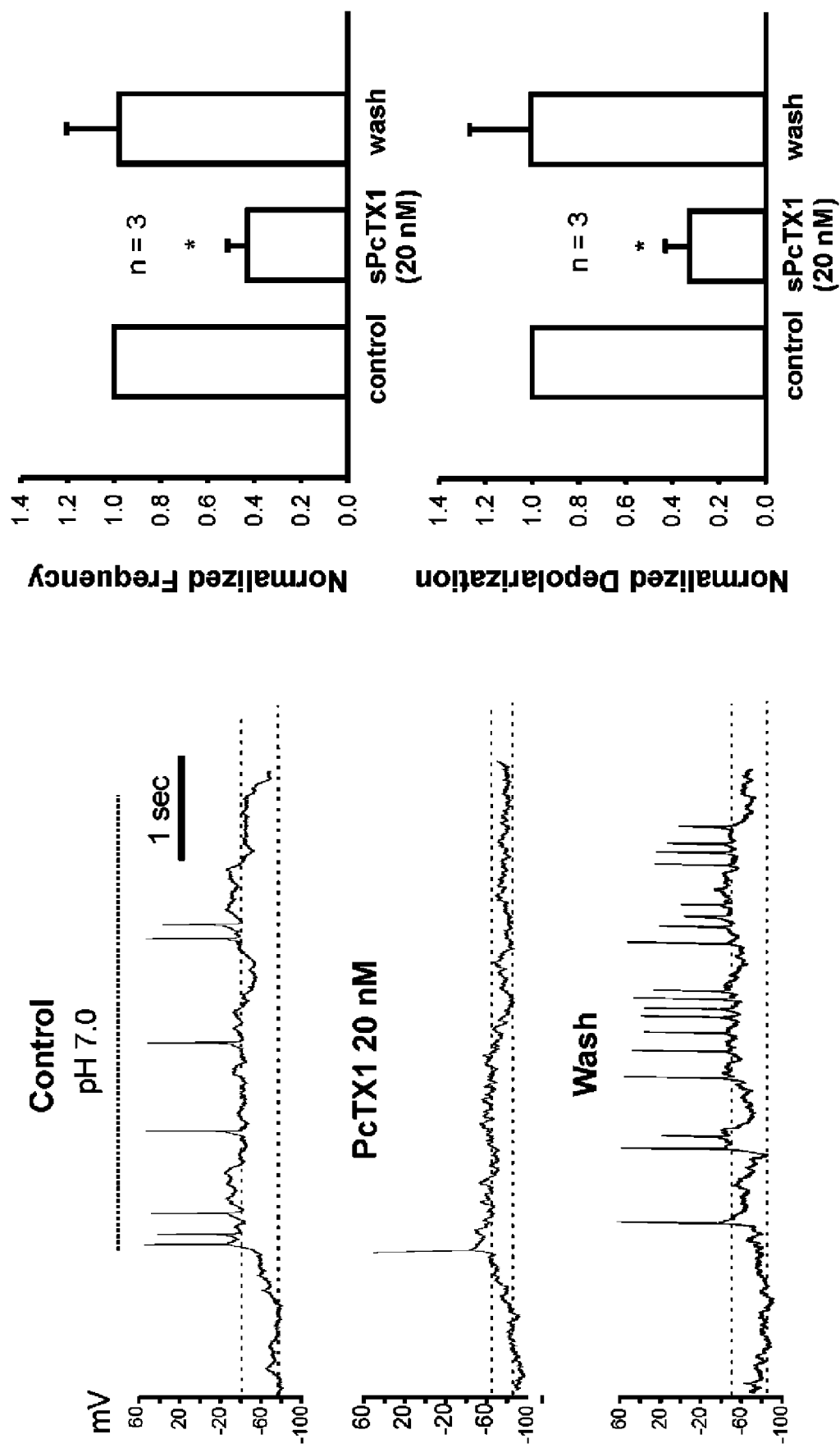

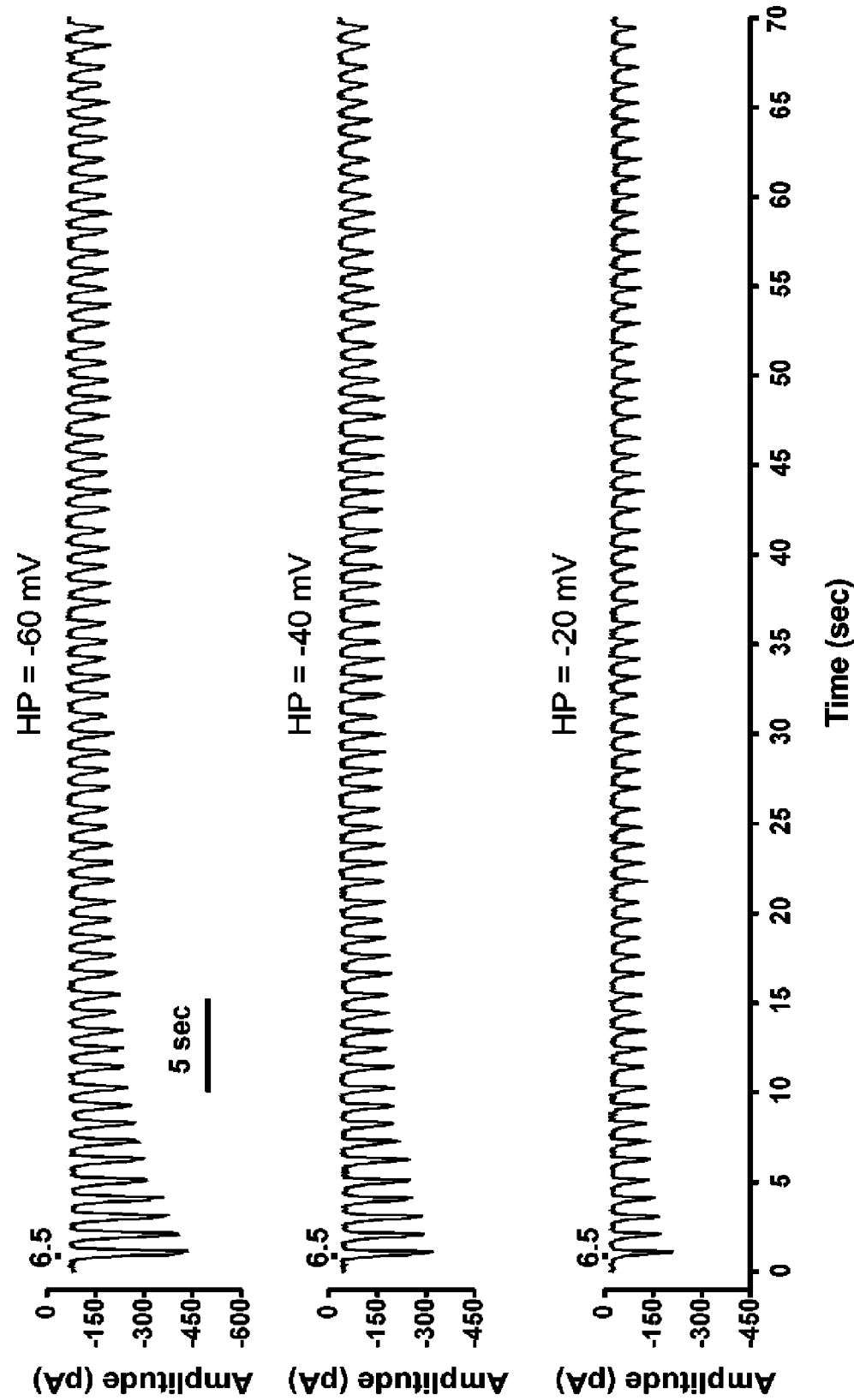

SYSTEM FOR SEIZURE SUPPRESSION

CROSS-REFERENCES TO PRIORITY APPLICATIONS

This application is based upon and claims the benefit under 35 U.S.C. §119(e) of U.S. Provisional Patent Application Ser. No. 60/860,522, filed Nov. 21, 2006, and U.S. Provisional Patent Application Ser. No. 60/959,987, filed Jul. 17, 2007. Each of these patent applications is incorporated herein by reference in its entirety for all purposes.

GOVERNMENT LICENSE RIGHTS

This invention was made with U.S. Government support from National Institutes of Health R01 grants NS49470, NS47506, and NS50610. The U.S. Government thus may have certain license rights in the invention.

BACKGROUND

Epilepsy is a common neurological disorder that affects people of all ages. In children, epilepsy is the second leading cause of disability and death. Across all ages, 2.7 million Americans have epilepsy, which is a greater incidence than for multiple sclerosis, cerebral palsy, muscular dystrophy, and Parkinson's disease combined.

Epilepsy is a chronic neurological disorder characterized predominantly by recurrent and unpredictable interruptions of normal brain function, called epileptic seizures. An epileptic seizure is a transient occurrence of signs and/or symptoms resulting from abnormal neuronal activity in the brain that is usually excessive, synchronous, or both. Epilepsy is not a singular disease but a variety of disorders reflecting underlying brain dysfunction that may result from many different causes. The disorder may be caused, for example, by abnormality of brain circuitry, imbalance of neurotransmitters, trauma to the brain, infection, or a combination of factors. Regardless of seizure type and cause, the two hallmarks of seizure generation are hyperexcitability of neurons and/or hypersynchrony of neural circuits.

Current epilepsy therapies rely on surgical removal of epileptic foci (e.g., a portion of the hippocampus) or pharmacological intervention with antiepileptic drugs (AEDs). However, current AEDs do not provide an effective prevention or true pharmacotherapeutic cure for epilepsy. In particular, a third of epilepsy patients are not free of seizures despite drug therapy, and in about 30% of patients, the disorder develops into a form with resistance to current AEDs. Furthermore, current AEDs may have various side effects that substantially limit their use. Therefore, new drugs for suppressing epileptic and non-epileptic seizures and methods of screening for new anti-seizure drugs are needed.

SUMMARY

The present teachings provide systems, including methods and compositions, for seizure suppression, such as inhibition of epileptic seizures. In some embodiments, the methods may provide a screen for anti-seizure drugs. One or more compositions may be selected based on an ability to affect a response of biological cells to a change in extracellular pH and/or to affect an activity of at least one acid sensing ion channel (ASIC). Based on the one or more compositions selected at least one drug candidate may be assayed for inhibition of seizure-like electrical activity and/or seizures. In some embodiments, the methods and compositions may, respectively, administer and provide an effective amount of PcTX1, a peptide derivative of PcTX1, amiloride, an amiloride derivative, or a combination thereof to a subject prone to seizures and/or having a seizure, in order to suppress seizure activity.

BRIEF DESCRIPTION OF THE DRAWINGS

FIGS. 5A-5D are a collection of graphs presenting exemplary electrophysiological data collected from mouse hippocampal slices exhibiting repetitive seizure-like electrical activity evoked in low magnesium by a single electrical stimulation or spontaneously, with the effect of amiloride, PcTX1 venom, or synthetic PcTX1 peptide on the seizure-like electrical activity being tested.

FIGS. 7A-7E are a set of graphs presenting exemplary electrophysiological data collected from hippocampal slices provided by wild-type (WT) and ASIC1$^{-/-}$ mutant ("ASIC1 KO" (knockout)) mice and exhibiting seizure-like bursting activity (after-discharges) induced by high-frequency stimulus trains, with the effect of amiloride and PcTX1 on the seizure-like electrical activity being tested.

FIGS. 9A-9C are a collection of graphs presenting exemplary electrophysiological data collected by patch-clamp recordings from mouse hippocampal neurons exposed to a drop in extracellular pH, in the presence or absence of amiloride or synthetic PcTX1.

FIGS. 10A and 10B are a collection of graphs presenting exemplary electrophysiological data collected by patch-clamp recording from neurons repetitively exposed to two different extracellular pHs.

DETAILED DESCRIPTION

Figure 1:
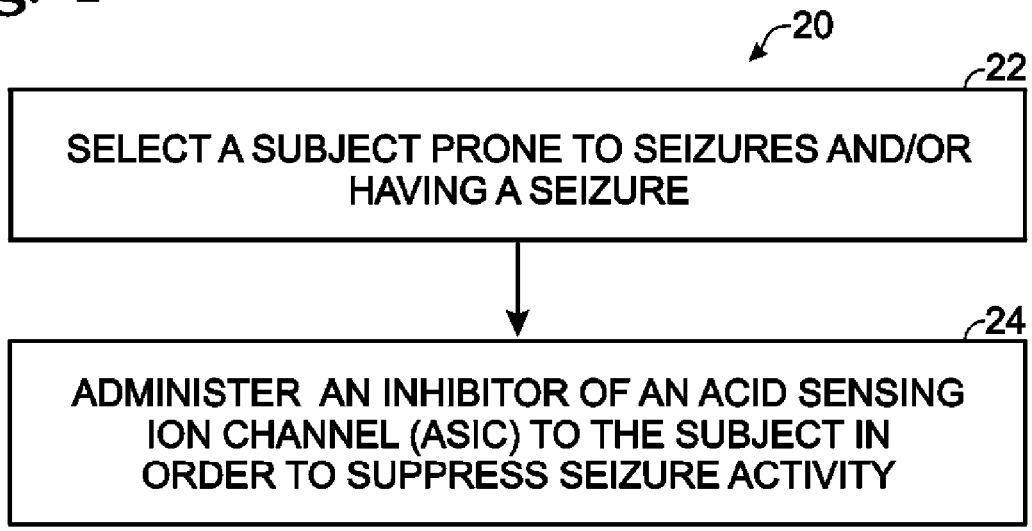
FIG. 1 is a flowchart of an exemplary method of treating seizures, in accordance with aspects of the present teachings.

The present teachings provide systems, including methods and compositions, for seizure suppression, such as inhibition of epileptic seizures.

The methods may provide a screen for anti-seizure drugs. One or more compositions may be selected based on their ability to affect, such as inhibit, a response of biological cells to a change in extracellular pH, such as one or more drops in extracellular pH, and/or to affect such as selectively inhibit, at least one acid sensing ion channel (ASIC). In some examples, the one or more compositions may be one or more chemical compounds selected based on results of testing a plurality of chemical compounds in an assay designed to measure a cellular response to a drop in extracellular pH and/or to measure an ASIC activity. The cellular response and/or ASIC activity may be detected optically and/or electrically, among others. In any event, at least one drug candidate may be obtained based on the one or more compositions selected. The at least one drug candidate may have the same chemical structure as at least one (or all) of the one or more compositions selected and/or may be or include a structural derivative or a set of structural derivatives that are obtained based on at least one of the compositions selected. The at least one drug candidate may be assayed for inhibition of experimentally induced seizure-like electrical activity in cells and/or tissues and/or for inhibition of seizures in animals, such as a non-human test species or in humans.

The methods also or alternatively may provide a treatment for seizures by administration of an effective amount of a drug to a subject prone to seizures and/or having a seizure, in order to suppress seizure activity. The drug may include PcTX1 (peptide), a peptide derivative of PcTX1, amiloride, an amiloride derivative or a combination thereof. Alternatively, or in addition, the drug may correspond to a drug candidate identified in a method of screening for anti-seizure drugs, such as described in the preceding paragraph and elsewhere in the present teachings.

The systems of the present teachings result from data relevant to brain acidosis. Brain acidosis is a common feature of acute neurological diseases including epileptic seizures and may play an important role in the pathophysiology of neuronal injury. While the pathogenic role of acidosis in brain ischemia has received substantial attention, cellular and molecular mechanisms underlying acid signaling in the epileptic brain and in seizure-induced brain injury have not been described previously.

The present teachings (e.g., see Examples 1-4) provide data on the role of ASICs in seizure model systems. In a cell culture model of epilepsy, brief withdrawal of the NMDA antagonist kynurenic acid induced high frequency bursts and synchronous depolarization shifts. Amiloride a nonspecific blocker of ASICs, and PcTX1, a specific blocker of ASIC1a, both significantly inhibited the increase of neuronal firing and the sustained membrane depolarization. In hippocampal slices, high frequency electrical stimulation or removal of extracellular $Mg^{2+}$ produced spontaneous seizure-like bursting. Bath perfusion of amiloride significantly decreased the amplitude and the frequency of the seizure-like bursting. PcTX1 also showed inhibition of seizure-like bursting. In contrast to the slices from wild-type animals, slices prepared from the brains of ASIC1a knockout mice demonstrated reduced sensitivity to low $[Mg^{2+}]_o$-induced seizure activity. Finally, the present teachings show an effect of ASIC blockade in an in vivo model of epilepsy. Intra-amygdala injection of kainic acid (KA) induced sustained polyspike activity, as measured by EEG, followed by dramatic injury of CA3 neurons. Intracerebroventricular injection of PcTX1 reduced both electrographic seizure activity and CA3 neuronal injury. Consistent with the in vitro model, ASIC1a knockout mice appeared to be resistant to KA-induced seizure activity and neuronal CA3 injury in vivo. Together, the data presented herein strongly support the hypothesis that activation of ASICs, particularly the ASIC1a channel, is involved in the generation of seizure activity and seizure-mediated neuronal injury. Accordingly, compositions that inhibit the activity of ASICs should be antiepileptic.

FIG. 1 shows a flowchart of an exemplary method 20 of treating seizures. A subject prone to seizures and/or having a seizure may be selected, indicated at 22. In some embodiments, the subject may be an individual diagnosed as having epilepsy. An effective amount of an inhibitor of at least one acid sensing ion channel (ASIC) may be administered to the subject in order to suppress seizure activity, indicated at 24. In some embodiments, the inhibitor may be PcTX1 (peptide), a peptide derivative of PcTX1, amiloride, an amiloride derivative, or a combination thereof.

Further aspects of the present teachings are presented in the following sections, including (I) definitions, (II) subject selection, (III) drug administration, (IV) screening for anti-seizure drugs, and (V) examples.

I. Definitions

The term "seizure," as used herein, means an abnormal electrical activity in the brain that results in at least one clinical symptom. The electrical activity may be characterized by hypersynchrony, hyperactivity, and/or hyperexcitability of neurons in a portion or all of the brain. Exemplary symptoms produced by seizures may include sudden and involuntary muscle contraction (e.g., convulsions), numbness of a part or all of the body, memory loss, loss of consciousness, inability to concentrate, hallucinations, and/or the like. Seizures thus may affect motor, autonomic, cognitive, sensory (visual, auditory, olfactory, taste, feel), and/or emotional function, among others. Each seizure may be characterized either as an epileptic seizure, produced by epilepsy, or a non-epileptic seizure with any other cause.

The term "seizure activity," as used herein, means the abnormal electrical activity associated with at least a portion of one or more seizures.

The term "epilepsy," as used herein, means any chronic neurological disorder characterized by recurrent seizures. Each seizure may appear to be unprovoked or may be triggered or provoked by stress, anxiety, sleep deprivation, illness, chemical exposure (e.g., drug abuse or alcohol consumption), photic stimulation (e.g., a flashing/flickering light), and/or the like. The disorder may have a cause that is unknown or may be caused, for example, by head trauma, a brain tumor, a genetic predisposition, an infection, a developmental defect, or any combination thereof, among others. Exemplary types of epileptic seizures include partial or focal onset seizures, which are localized (at least initially) within the brain, and generalized seizures, which are distributed widely within the brain. Partial seizures may be further categorized as simple partial seizures, which do not affect consciousness, and complex partial seizures, which do affect consciousness. Generalized seizures, which produce a loss of consciousness, may include absence, atonic, clonic, myoclonic, tonic, and tonic-clonic seizures, among others. Exemplary seizure syndromes that may be treated include benign focal epilepsies of childhood, childhood absence epilepsy, fetal alcohol syndrome, frontal lobe epilepsy, infantile spasms, juvenile myoclonic epilepsy, Lennox-Gastaut syndrome, occipital lobe epilepsy, or any combination thereof, among others. Epilepsy and/or an epileptic seizure may be diagnosed by any suitable technique or combination of techniques including electroencephalography (EEG), magnetoencephalography, magnetic resonance imaging (MRI), positron emission tomography (PET), single photon emission computed tomography (SPECT), or video-EEG, among others.

The term "to suppress one or more seizures," "to suppress seizure activity," and similar terms, as used herein, means to reduce the frequency of seizures; to reduce the severity, physical extent, and/or duration of at least one seizure; to substantially prevent at least one seizure; or any combination thereof. Seizure suppression for a particular subject may be measurable directly from the subject (e.g., if a seizure is in progress during treatment) and/or, more typically, may be a statistically predicted outcome based on results from controlled tests or clinical trials with a group of subjects.

The term "seizure-like electrical activity," as used herein, means any electrical activity elicited from isolated cells, a tissue explant, or the brain, in which the electrical activity serves as a model for the electrical activity present in an actual seizure. Seizure-like electrical activity may be elicited by exposing cells, tissue, or the brain to electrical stimulation (kindling) (e.g., repetitive and/or high frequency electrical stimulation), a chemical substance(s) (e.g., picrotoxin or kainic acid) (or removal thereof (e.g., removal of kynurenic acid)), photic stimuli (e.g., a flashing/flickering light), or altered ionic conditions (e.g., reduced extracellular $Mg^{2+}$) Further examples of mechanisms for eliciting seizure-like electrical activity from cells, hippocampal explants, and the intact brain are described below in Example 1.

The term "drug," as used herein, means a substance, other than food, intended for use in the treatment, prevention, diagnosis, cure, and/or mitigation of a disease, disorder, or condition in humans or animals. The drug may be or include a bioactive agent or a mixture of bioactive agents for external or internal use. A "candidate drug," as used herein, means a prospective drug that has not yet been tested fully (or at all) and/or formally approved for use as a drug.

The term "subject," as used herein, means a many-celled vertebrate or invertebrate organism from the animal kingdom. The subject thus may be a person (also termed an individual or a human) or a non-human animal (hereafter, termed only an "animal"). Exemplary animals include laboratory animals, farm animals, pets, or sport animals, among others. An animal subject thus may, for example, be a rodent (such as a mouse, rat, hamster, guinea pig), dog, cow, horse, non-human primate, bird, amphibian, reptile, fish, insect, or the like. Non-human subjects may be test species, that is, animals for testing the effect of a composition, chemical compound, or candidate drug, generally prior to human clinical trials and/or use as an approved drug in humans and/or animals. Alternatively, non-human: subjects may be drug recipients after a drug has been tested and/or approved, such as for treatment in a veterinary setting.

The term "prone to seizures," as used herein with respect to a subject, means that the subject has been diagnosed as having epilepsy; has a history of seizures, that is, has already suffered one or more seizures; has a disease, disorder, or condition that is known or expected to substantially increase the probability of having a seizure; or any combination thereof.

The term "having a seizure," as used herein with respect to a subject, means that the subject currently is suffering a seizure, with abnormal electrical activity in the brain, and is presenting one or more symptoms of seizure. Since seizures have a wide range of durations, subjects having a seizure of longer duration, such as status epilepticus, may be candidates for treatment to attenuate or stop a seizure that is already in progress.

The term "chemical substance," as used herein, means a material having a definite chemical makeup. A chemical substance thus may be a chemical element or a chemical compound.

The term "chemical compound," as used herein, means a substance consisting of two or more elements chemically bonded in a fixed proportion by mass.

The term "composition," as used herein, means a chemical substance or a mixture of chemical substances. Accordingly, a composition may be or include one or more chemical elements and/or one or more chemical compounds.

The term "structural derivative" or "derivative," as used herein with respect to a first chemical compound, means a second chemical compound with a chemical structure that is related to the chemical structure of the first chemical by substitution at one or more positions. The terms "derivative" or "structural derivative" indicate a formal relationship between the chemical structures of the first and second chemical compounds, independent of when and how the first and second chemical compounds were designed and synthesized relative to each other. In other words, according to this definition, if one compound is a derivative of another compound, then both compounds are derivatives of each other.

The term "effective amount," as used herein with respect to a substance, means a quantity of the substance that produces a therapeutic response in subjects to which the quantity has been administered. The therapeutic response may be produced in any statistically significant proportion of the subjects relative to those receiving placebo, such as at least about 25%, 50%, or 75% of the subjects receiving the effective amount. The effective amount may be given to a subject in a single dose or collectively via a plurality of doses.

The term "pharmaceutical preparation," is used herein is any pharmaceutically acceptable mixture or composition that contains an effective amount of a drug for administration to a subject in one or more doses. The term "pharmaceutically acceptable," as used herein, means approved by a regulatory agency of a federal or state government or listed in the U.S. Pharmacopeia or other generally recognized pharmacopeia for use in animals, and more particularly, in humans.

The term "cells" or "biological cells," as used herein, mean the elementary units of which all known life forms are composed. The cells may be prokaryotic and/or eukaryotic cells. If eukaryotic cells, the cells may be from any suitable organism, such as cells that are human, non-human primate, murine (mouse), bovine (cow), porcine (pig), ovine (sheep), canine (dog), feline (cat), equine (horse), or the like. The cells may be neurons from the brain or elsewhere in the nervous system. Exemplary neurons that may be suitable include hippocampal neurons and/or cortical neurons, among others. Alternatively, or in addition, the cells may be or include non-neurons. The cells may be provided by an established cell line, such as tumor cells that are transformed and/or immortalized to facilitate culture, or may be primary cells isolated from tissue, such as by disrupting cell-cell contacts of the tissue, generally without immortalization and/or transformation. Furthermore, the cells may be stem cells (e.g., totipotent stem cells, pluripotent stem cells, embryonic stem cells, adult stem cells, and/or the like) or differentiated cells. In some embodiments, the cells may be neurons or a non-neuronal cell type engineered for use in an ASIC assay. For example, the cells may be modified by introduction of foreign nucleic acid to express at least one exogenous ASIC protein (e.g., ASIC1a, ASIC1b, ASIC2a, ASIC2b, ASIC3, ASIC4, or any combination thereof, among others). Cells engineered for use in an ASIC assay may be an established cell line or primary cells.

The term "acid sensing ion channel" or "ASIC," as used herein, means any current or future member(s) of the family of proton-activated ion channels. The six current members, ASIC1a, ASIC1b, ASIC2a, ASIC2b. ASIC3, and ASIC4 belong to the amiloride-sensitive epithelial $Na^+$-channel/degenerin superfamily. Further aspects of ASICs are described below in Example 6.

The term "ASIC assay" or a grammatical equivalent thereof, as used herein, means any test designed to directly or indirectly measure an activity, such as ion transport, of one or more ASICs. The ASIC assay may provide a relatively direct measurement of ASIC activity, such as via an electrical measurement, or may provide a relatively indirect measurement of ASIC activity, such as via detection of a consequence of ion transport. The consequence of ion transport may be an immediate consequence or a consequence substantially downstream of the ion transport. ASIC assays may be performed on ASICs disposed in whole cells, particularly, live cells, or on cell-free ASICs that are not disposed in whole cells, such as ASICs disposed in isolated membrane patches.

The term "sample mixture," as used herein, means any mixture that includes a composition to be tested along with one or more reagent (e.g., cells, diluents, buffers, dyes, reactants, substrates. etc.) that permit or facilitate testing.

The term "ASIC inhibitor" or a grammatical equivalent thereof, as used herein, means any chemical substance and/or composition capable of substantially reducing (including eliminating) an activity of at least one ASIC, such as the ability of one or more ASICs to conduct an ion current in any suitable ASIC assay. An ASIC inhibitor may reduce the magnitude of the ion current and/or the duration of the ion current, among others. Substantial reduction of the ion current may be a reduction in magnitude and/or duration of at least about 25%, 50%, 75%, or 90%, among others. The ASIC inhibitor also or alternatively may affect the sensitivity of one or more ASICs to activation by protons (pH) and/or may increase the steady-state inactivation or the rate of ASIC desensitization after activation. The ASIC inhibitor may be selective or specific for inhibition of ASIC proteins relative to other ion channels, that is, may be capable of inhibiting one or more (or all) ASICs to the substantial exclusion of most (selective) or all (specific) non-ASIC channels. Furthermore, the ASIC inhibitor may be selective/specific or nonselective/nonspecific for inhibition within the ASIC family. If specific for inhibition within the ASIC family, the ASIC inhibitor may be capable of inhibiting one or more ASICs (e.g., ASIC1a only or ASIC1a plus ASIC1b only) to the substantial exclusion of the other ASICs.

The term "PcTX1," as used herein, means the spider toxin peptide Psalmotoxin 1 from the tarantula species Psalmopoeus cambridgei (Pc). The toxin peptide may be used without substantial purification as part of venom from the tarantula species, may be purified from the venom, may be synthesized chemically, or may be biosynthesized by an engineered organism, among others. At a concentration where PcTX1 is effective for inhibiting ASIC1a, the inhibition of ASIC1a has been reported to be specific relative to the other ASIC family members.

The term "PcTX1 derivative," as used herein, means a peptide with a chemical structure formally related to PcTX1 and distinguished from PcTX1 by one or more amino acid substitutions, deletions, and/or insertions. A PcTX1 derivative may be produced de novo or, in some cases, may be synthesized by chemical modification of PcTX1. Exemplary derivatives of PcTX1 may include deletions of one or more amino acids, insertions of one or more amino acids, substitution of one or more amino acids with other amino acids or with non-amino acids, or any combination thereof. A PcTX1 derivative may have an amino acid sequence with at least about 20%, 40%, 60%, 80%, or 90% amino acid ideentity withh the amino acid sequence of PcTX1, when the sequences are aligned.

The term "amriloride," as used herein, means a pyrazine derivative that includes a guanidinium moiety, and more particularly having the systematic (IUPAC) name 3,5-diamino-6-chloro-N(diaminomethylidene)pyrazine-2-carboxamide, and corresponding to the structural formula

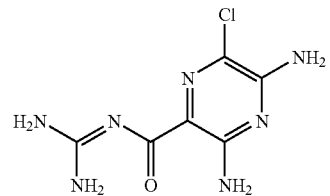

Amiloride may be in any suitable nonionic form or ionic form (i.e., as a salt). Amiloride is a blocker of ASICs, although its effect is not specific to ASICs. In particular, over a concentration range at which amiloride is effective for blocking ASICs, amiloride may inhibit other membrane transport proteins, such as $Na^+/Ca^{2+}$ exchangers, $Na^+/H^+$ exchangers, and glutamate-operated cationic channels.

The term "amiloride derivative," as used herein, means any structural derivative of amiloride, and more particularly, a chemical compound that is structurally related, to amiloride and distinguished from amiloride by substitution at one or more positions. In some embodiments, an amiloride derivative is described by the structural formula

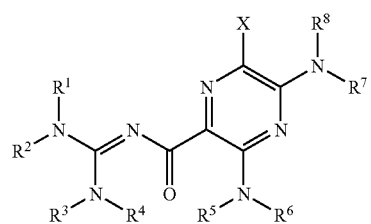

where the X substituent is a halogen moiety. X is typically fluoro, chloro, or bromo. In some embodiments, X is chloro.

The amino substituents $R^1$-$R^8$ may be selected independently from H, alkyl having 1-12 carbons, arylalkyl having 7-13 carbons, aryl, or heteroaryl. If one or more of substituents $R^1$-$R^8$ is alkyl or arylalkyl, the alkyl portion of each alkyl or arylalkyl substituent may be optionally and independently further substituted one or more times by halogen, hydroxy, alkoxy having 1-6 carbons, aryl, heteroaryl, amino, alkylamino having 1-6 carbons, dialkylaminio having 2-12 carbons, carboxylic acid, or an ester formally derived from carboxylic acid and an alcohol having 1-6 carbons. If one or more of substituent $R^1$-$R^8$ is aryl, arylalkyl, or heteroaryl the aromatic portion of each aryl, arylalkyl, or heteroaryl substituent may be independently further substituted one or more times by halogen, alkyl having 1-6 carbons, amino, alkylamino having 1-6 carbons, dialkylamino having 2-12 carbons, carboxylic acid, or an ester formally derived from carboxylic acid and an alcohol having 1-6 carbons. In some embodiments, each of substituents $R^1$-$R^8$ is independently selected from H, alkyl having 1-6 carbons, and arylalkyl, each of which may be further substituted as discussed above.

In some embodiments, the amiloride derivative is described by the structural formula

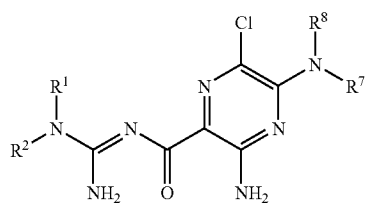

where $R^1$, $R^2$, $R^7$ and $R^8$ are independently H, alkyl having 1-6 carbons, or arylalkyl having 7-13 carbons.

The term "affect a response of cells," as used herein, means inhibiting (i.e., reducing, slowing, shortening, blocking, etc.), enhancing (i.e., increasing, speeding, lengthening, unblocking, etc.), or otherwise altering any characteristic change in the cells. The change may, for example, be a change in membrane potential, current across the membrane, calcium concentration, protein phosphorylation, protein dephosphorylation, reporter gene activity. subcellular localization of a cellular constituent, or any combination thereof among others.

The term "administer," as used herein with respect to a drug or drug candidate and a subject, means to give or apply the drug or drug candidate to the subject such that the drug or drug candidate can exert its bioactive effect, if any, on the subject. Accordingly, administering a drug may include delivering the drug to a subject by any suitable route, including injection, ingestion, inhalation, topical application, or any combination thereof, among others. Injection may be performed subcutaneously, intradermally, intravenously, intra-arterially, intrathecally, epidurally, subdurally, intracerebroventricularly (i.e., into the brain), intraocularly, intraperitoneally, intra-synovially, or any combination thereof, among others. Injection may, for example, be via a needle or may be with a needle-free injector. Ingestion may be via a liquid formulation, a capsule, a tablet, or the like. Inhalation (or topical application to epithelia in the body) may be via an inhaler, atomizer, sprayer, or the like, and may involve a spray or particles/droplets of any suitable size, such as a spray or particles/droplets configured or sized for delivery to epithelia in the nose, mouth, pharynx, larynx, or lungs, among others. Topical application may involve placement of the drug onto an epithelial layer for trans-epithelial uptake. Exemplary epithelia for topical application may include external application to the skin or a wound thereof (i.e., direct placement onto the epidermis, dermis, hypodermis, or exposed wound tissue, among others). Other exemplary epithelia for topical application may include rectal, vaginal, urethral, oral, nasal, or ocular epithelia, or any combination thereof. Topical application may be facilitated by formulating the drug as an ointment and/or by placing the drug onto a dermal patch.

The term "selecting," as used herein, means to choose, identify, and/or designate one or more members from a set according to one or more criteria. Selecting may be at least substantially or exclusively a cognitive process. Selecting may be performed by one person, at least in part by group discussion or consensus, partly or exclusively by a digital processing device (e g., a computer), or any combination thereof, among others.

The term "obtaining," as used herein, means to come into possession of and/or to bring or cause to fall under the influence of by any suitable means. Accordingly, a chemical compound or composition that is obtained may, for example, be purchased, synthesized, extracted, purified fetched (e.g., from a shelf or stockroom), borrowed, or any combination thereof, among others.

The remaining terms used in the present teachings and not explicitly defined herein should be given their ordinary and customary meaning dictated by the context in which they are used.

II. Subject Selection

A subject may be selected to receive an anti-seizure drug. Selection may be performed by any suitable person and/or mechanism. For example, selection may be performed by a medical practitioner, such as a doctor, a nurse, a veterinarian, a medical counselor, and/or the like. Alternatively, or in addition, selection may be performed by the subject himself/herself (e.g., if the drug is available "over the counter" without a prescription from a medical practitioner). In some embodiments, selection may be performed exclusively by, or with the assistance of, a digital processing device (e.g., a computer) that receives data about the subject and analyzes the data using an algorithm to determine whether or not the subject should be selected to receive the anti-seizure drug or drug candidate.

The subject may be selected based on any suitable criteria. For example, the subject may be selected for being prone to seizures. Selection thus may be based on a medical history of the subject, a previous occurrence of at least one seizure, a clinical test result(s) predicting a relatively higher risk for the subject to suffer a seizure in the future, a present medical condition placing the subject at risk for a seizure, or any combination thereof, among others. The medical history may be a written record or an oral communication of the subject's past medical conditions and/or clinical test results. In some embodiments, the subject may be selected because the subject is currently experiencing a seizure or has one or more signs and/or symptoms indicating a seizure is occurring or is about to occur.

In some cases, subjects may be selected to receive a drug candidate, to test the efficacy of the drug candidate in humans or non-human subjects. The subjects thus may be selected according to any of the criteria above and/or to provide a representative population for clinical trials or animal testing.

III. Drug Administration

A drug may be administered to a subject in order to suppress one or more seizures and/or seizure activity. The drug may be administered by any of the delivery routes and mechanisms described above in Section I. The drug may be administered by a medical practitioner, may be self-administered by the subject, or may be administered by any other person.

Any suitable drug may be administered including PcTX1, a PcTX1 derivative, amiloride, an amiloride derivative, a drug identified in and/or suggested by a screen for ASIC inhibitors, or any combination thereof, among others. In exemplary embodiments, the drug may be amiloride or an amiloride derivative administered by injection. In other exemplary embodiments, the drug may be PcTX1 or a PcTX1 derivative administered by injection or nasally (i.e., to the nasal cavity). In some embodiments, nasal administration may promote passage of the drug to the brain.

The NMDA subtype of glutamate receptors may be involved in seizure-induced brain injury. Activation of ASICs with subsequent membrane depolarization may indirectly facilitate the activation of NMDA receptor channels thus contributing to NMDA receptor-mediated injury. On the other hand, activation of NMDA receptors and subsequent phosphorylation by CaMKII may enhance the activation of ASICs. Blocking ASIC or NMDA activities may therefore induce neuroprotection. Accordingly, more effective seizure treatments may be provided by administering, to a subject, both an ASIC inhibitor and an antagonist for NMDA receptor channels, such as amantadine, dextromethorphan, dizocilpine (MK-801), ibogaine, ketamine, memantine, nitrous oxide, phencyclidine, tramadol, or a combination thereof, among others. The ASIC inhibitor and NMDA receptor antagonist may be administered in the same pharmaceutical preparation or in distinct pharmaceutical preparations. Furthermore, the inhibitor and antagonist may be administered by the same or different delivery mechanisms.

IV. Screening for Anti-Seizure Drugs

Figure 2:
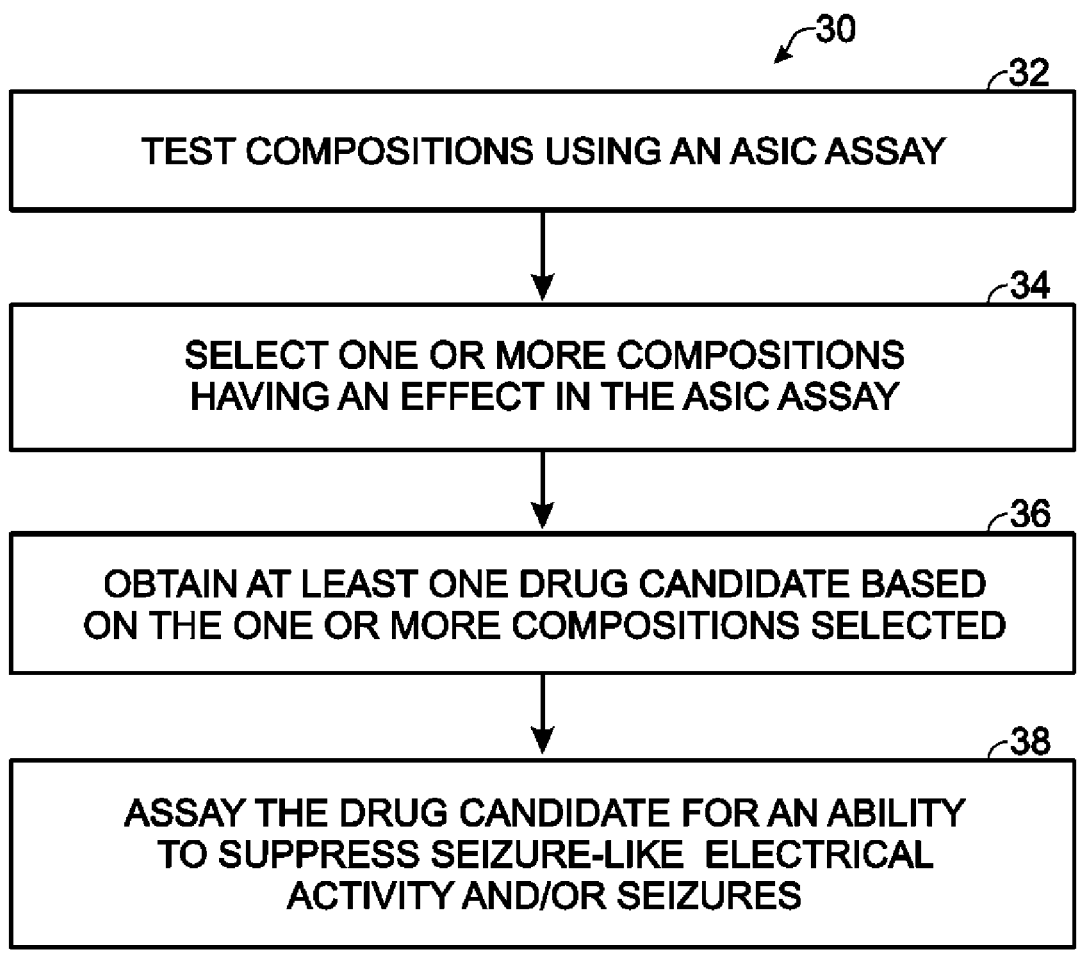
FIG. 2 is a flowchart of an exemplary method of screening for anti-seizure drugs, in accordance with aspects of the present teachings.

The present teachings provide a method of screening for anti-seizure drugs. FIG. 2 shows a flowchart of an exemplary method 30 of screening. The steps presented in FIG. 2 may be performed in any suitable order, in any suitable combination, and any suitable number of times. Furthermore, any combination of the steps presented in FIG. 2 may be conflated with any other step(s) described elsewhere in the present teachings to provide a screening method.

Compositions may be tested using an ASIC assay, indicated at 32. The compositions may correspond to a set or library of compositions, with the set/library including any suitable number of compositions, such as at least 2, 10, 100, 1,000, 10,000, or 100,000 compositions. Each composition may be or include a different chemical substance and/or chemical compound (or a different mixture of chemical substances/compounds), such that the set/library may be described as a set/library of chemical substances or compounds (e.g., a compound library). Any suitable chemical compounds may be screened, such as a library of small organic molecules (e.g., with an average molecular weight of less than 5 or 2 kilodaltons), peptides, nucleic acids, lipids, carbohydrates, known ion transport agonist/antagonists, or any combination thereof. Members of the library may be tested individually or as mixtures of chemical substances/compounds. In any event, to promote high throughput, the compositions may be tested in an array format, such as with microplates providing an array of wells for holding sample mixtures. Exemplary microplates that may be suitable include microplates with 24, 96, 384, and 1536 wells. In some embodiments, two or more members of a library may be tested individually and in parallel on cells using a multiplexed patch-clamp system, such as via planar patch clamp electrodes disposed in an array.

The compositions may be tested as a part of sample mixtures in any suitable assay that reflects a response of the sample mixtures to a change in pH and/or that reflects an ASIC activity in the sample mixtures. The assays thus may be performed with cells or in a cell-free system. The change in pH may be a reduced pH, such as a reduced extracellular pH. Sample mixtures used for testing thus may be exposed to a drop in pH and/or to a pH that is less than physiological pH (e.g., less than pH 7.4). A reduced pH may be imposed once or a plurality of times for each sample mixture. For example, the sample mixture may be exposed to a repetitively varying pH (such as at least, in order, a pH decrease, a pH increase, and a pH decrease), which may be suitable for identifying compositions that affect (e.g., enhance) ASIC desensitization resulting from a drop in pH and/or that affect (e.g., inhibit) recovery from ASIC desensitization when the pH is raised after the drop (e.g., see Examples 1 and 3). Repetitive changes in pH may be pulses of reduced pH, separated by intervals of increased pH. Each pulse of reduced pH may have any suitable length (duration), such as about 0.1-10, 0.2-5, or 0.5-2 seconds. In addition, each interval of increased pH may have any suitable length, such as about the same as, shorter than, or longer than the length of the reduced pH pulses. Furthermore, the pulses and/or intervals may be uniform or nonuniform. The pulses and/or intervals may have any suitable frequency, such as at least about 0.2, 0.5, 1, or 2 Hz, or 0.1-10, 0.2-5, or 0.5-2 Hz, among others.

A drop in pH may be imposed by any suitable technique, such as changing a fluid (e.g., media and/or buffer) in which the sample mixtures and/or cells thereof are disposed, to another fluid of lower pH, or by adding acid to or releasing protons in (e.g., by chemical reaction) the fluid, among others. The drop in pH for a sample mixture may be executed over any suitable time interval, such as a sudden, stepwise drop in pH (e.g., in less than 1 or 0.1 second), or a slower, more gradual drop in pH (e.g., in greater than one second). In exemplary embodiments, the pH of a sample mixture may be reduced by at least about 0.1, 0.2, 0.5, or 1.0 pH unit from the pH value of the sample mixture immediately prior to pH reduction and/or from physiological pH. In exemplary embodiments, one or more ASICs may be activated by dropping the pH of the sample mixture from 7.4 to 6.5 or 6.0, since an ASIC activity (e.g., an ASIC-mediated current) of readily detectable magnitude may be recorded at these pH values. In some embodiments, a smaller pH drop (e.g., from pH 7.4 to pH 7.2, 7.1, or 7.0) may be suitable because the smaller pH drop may be more analogous to the pH drop in an actual seizure. However, in some cases, the small activity of one or more ASICs with a smaller pH drop may make an ASIC activity difficult to quantify. Accordingly, in some embodiments, a current-clamp configuration may be used to study the effect of test compositions and/or candidate drugs on membrane depolarization induced by relatively small pH drops (e.g., to pH 7.1), which may be more relevant to epilepsy. Significant membrane depolarization (e.g., at least about 10 mV) may be induced by this pH drop.

Any suitable aspect of a sample mixture may be detected when the compositions are tested. Exemplary aspects may include an optical parameter, such as fluorescence, absorbance, polarization, scattering, reflection, refraction, birefringence, or any combination thereof. The optical parameter may be measured in a spatially resolved fashion from a sample mixture, such as by cell imaging, or may be measured from a sample mixture without spatial resolution of the sample mixture. The optical parameter may be measured at steady state (an end-point measurement) or while the optical parameter is changing, for example, in a time-resolved fashion (a kinetic measurement(s)). The optical parameter may be monitored over any suitable time interval or detected at any suitable time point after a change in pH, such as less than or greater than about 1, 10, or 60 seconds.

A pH drop sufficient to activate one or more ASICs may induce a membrane depolarization and/or may result in an influx of $Ca^{2+}$. Accordingly, in exemplary embodiments, testing may be performed on sample mixtures in the presence of a fluorescent dye, such as a calcium-sensitive dye (e.g., Fura-2, Fura-2AM, Fluo-3, Indo-1, Rhod-2, calcium-sensitive GFP (e.g., Cameleons), etc.), a membrane potential dye (e.g., Di-4-ANEPPS, RH421, $DiBAC_4(3)$, Tetramethylrhodamine ethyl/methyl ester perchlorate, etc.), or the like.

In some embodiments, an electrical parameter of a sample mixture may be measured electrically such as by patch-clamp analysis of cells and/or membranes. Recording in the patch-clamp analysis may be on a cell-attached patch, an inside-out patch, an outside-out patch, a perforated patch, or may be a whole cell recording, among others. Furthermore, the patch-clamp recording may be performed in a current-clamp or voltage-clamp mode.

Any suitable effect of the compositions may be tested using the ASIC assay. For example, testing may measure an ability, if any, of each composition to inhibit ASIC activity and/or to inhibit a response of cells to a reduced extracellular pH.

One or more compositions having an effect in the ASIC assay may be selected, indicated at 34. The one or more compositions selected may correspond to one or more individual chemical compounds or at least one chemical compound mixture. If the one or more selected compositions correspond to at least one compound mixture, chemical compounds of the compound mixture may be tested individually using an ASIC assay and/or an assay for a cellular response to reduced pH, in order to identify individual compounds that affect either or both of the assays.

At least one drug candidate may be obtained based on the one or more compositions selected, indicated at 36. The at least one drug candidate may have the same chemical structure as at least one of the compositions selected or may be a structural derivative thereof. In some embodiments, a composition may be selected from the step of testing and then may be used to provide a structural basis for obtaining a set of one or more structural derivatives related to the composition.

The at least one drug candidate may be assayed for an ability to suppress seizure-like electrical activity and/or seizures, indicated at 38. Accordingly, the at least one drug candidate may be assayed in a seizure model system provided by isolated cells, tissue explants, and/or animals, and/or may be tested in a clinical trial.

Seizure-like activity may be provided by in vitro preparations (isolated cells and/or tissue explants) that offer a variety of options for studying the mechanisms of the generation, spread, and termination of seizures using methods that are difficult to employ under in vivo conditions. Particularly, in vitro models may permit precise control of temperature and extracellular environment. However, in vitro models generally lack the behavioral and motor components of clinical seizures. Therefore, in vitro models generally rely on "equivalents" of seizures (seizure-like activities) that have been observed in vivo. Such equivalents may be characteristic changes of electrical activity and/or the ionic environment.

The at least one drug candidate may be assayed on isolated cells. For example, primary neurons (or an established cell line) may be manipulated to provide seizure-like electrical activity as described elsewhere in the present teachings, such as below in Example 1. The ability, if any, of the at least one drug candidate to inhibit or otherwise affect the seizure-like electrical activity may be assayed, for example, using a patch-clamp technique. In some embodiments the at least one drug candidate may be a plurality of drug candidates assayed in parallel using a multiplexed patch-clamp system, such as with planar patch-clamp electrodes.

The at least one drug candidate may be assayed on tissue explants (e.g., hippocampal or cortical slices) from brain with seizure-like activity induced by exposure to electrical stimulation, a pharmacological agent (e.g., picrotoxin or kainic acid), a change in ionic environment (e.g., a switch to low $Mg^{2+}$), a combination thereof, or the like. Reduced $Mg^{2+}$ may induce seizure-like bursts and is a commonly used in vitro epilepsy model. In this model, removing $Mg^{2+}$ from artificial CerebroSpinal Fluid (aCSF) may induce spontaneous and triggered interictal-like bursting, followed by spontaneous ictal-like events and finally periodic clustered bursts. The ictal-like events may consist of a tonic firing phase and a phase of clustered burst discharges resembling the tonic and clonic phases of seizures. This model may be clinically relevant because low levels of $Mg^{2+}$ may be associated with human epilepsy and because this model has been used to test the effect of antiepileptic agents. The use of tissue explants may have advantages over cultured cells, including (1) more options for inducing seizure-like activity, as described above and elsewhere in the present teaching, and/or (2) more choices for measuring the efficacy of a drug candidate, such as electrophysiological measurements with electrodes, staining the explant to determine the extent of injury (e.g., with propidium iodide), performing an enzyme assay on the explant (e.g., lactate dehydrogenase release to measure cell death), or the like. Further aspects of the use of tissue explants from brain are described below in Example 1.

The at least one drug candidate may be assayed in animals (e.g., mice) using electrical stimulation (kindling), photic stimulation (e.g., a flashing/flickering light), or pharmacological induction as models of epileptogenesis.

A common pharmacological model that may be employed, the kainic acid (KA) model, may be generated by intrahippocampal, intraamygdaloid, or intracerebroventricular administration of one or more doses of kainic acid (KA). The KA model may mimic the pathogenesis of human mesial temporal lobe epilepsy, a common form of human focal epilepsy, which is frequently associated with progression to chronic intractable, drug resistant epilepsy. As a primary consequence of KA injection, status epilepticus may be elicited, which in turn may lead to a characteristic pattern of hippocampal cell death (primarily the CA3 region). The KA model may be well suited to study epileptogenesis through electroencephalographic (EEG) monitoring of seizure activities and evaluation of resultant hippocampal cell death. For example, EEG monitoring (continuous or periodic, among others) may be performed on the animals. The percentage of time that EEG recordings show polyspike (type-4) activity may be quantified. The type-4 EEG activity may correlate best (e.g., linearly) with seizure-induced brain injury. Animals injected with amiloride, PcTX1, or an antiepileptic drug may be used as positive controls for comparison with drug candidates being assayed. Amiloride, PcTX1, and a drug candidate suitable for selection as an anti-seizure drug may show no or reduced type-4 activity, and less CA3 neuronal injury in the KA model. The brains of the animals also may be analyzed for seizure-induced injury, such as with an apoptosis stain (e.g., propidium iodide staining and/or a TUNEL assay), histological staining (e.g., with cresyl violet), and/or the like. Further aspects of the KA model and its use to assay ASIC inhibitors are described below in Example 1.

Any of the tests/assays described herein, or controls therefore, may be performed in the presence of inhibitors of selected membrane transport proteins. For example, blockers for various $Ca^{2+}$-channels (e.g., 5 μM nimodipine for L-type, 1 μM ω-conotoxin MVIIC for N— and P/Q-type, and 200 nM SNX482 for R-type $Ca^{2+}$-channels) and/or glutamate receptors (MK801 10 μM, CNQX 20 μM) may be added to prevent $Ca^{2+}$ entry from these sources during the activation of ASICs.

V. Examples

The following Examples describe selected aspects and embodiments of systems for seizure suppression. These Examples are included for illustration and to provide a framework for understanding aspects of the present teachings, and are not intended to limit or define the entire scope of the present teachings.

Example 1

Acid-Sensing Ion Channels in the Propagation of Epileptic Seizures and Seizure-Induced Brain Injury A. Summary Brain acidosis is a common feature of acute neurological aberrations including epileptic seizures (Chesler et al., 1992; Siesjo et al., 1996; Siesjo et al., 1986; Simon, 2006), and plays an important role in neuronal injury. While the pathogenic role of acidosis, and activation of acid-sensing ion channels (ASICs) (Waldmann et al., 1997), have received substantial attention in brain ischemia (Benveniste et al., 2005; Huang et al., 2004; Xiong et al. 2004), the role of ASICs underlying acid signaling in epileptic brain and in seizure-induced neuronal injury remains unexplored. In this Example, we show that mild acidosis, seen during epileptic seizures, induces membrane depolarization and excitation of CNS neurons through ASIC1a activation. In a cell culture model of epilepsy, ASIC1a blockade inhibits synchronous paroxysmal depolarization shifts. In hippocampal slice models of epilepsy, ASIC1a blockade suppresses low $Mg^{2+}$-induced epileptiform activity, and electrical stimulation-induced after-discharges. Consistent with pharmacologic blockade, slices from ASIC1 knockout mice show resistance to seizure induction. In a kainic acid model of status epilepticus, a common in vivo model of limbic seizures, intracerebroventricular injection of ASIC1a blockers, or ASIC1 gene knockout, reduces electrographic seizure activity and CA3 neuronal injury. Thus, activation of ASICs plays an important role in the propagation of epileptic seizures and constitutes a new and novel target for antiepileptic drug therapy.

B. Results

Figure 3A:
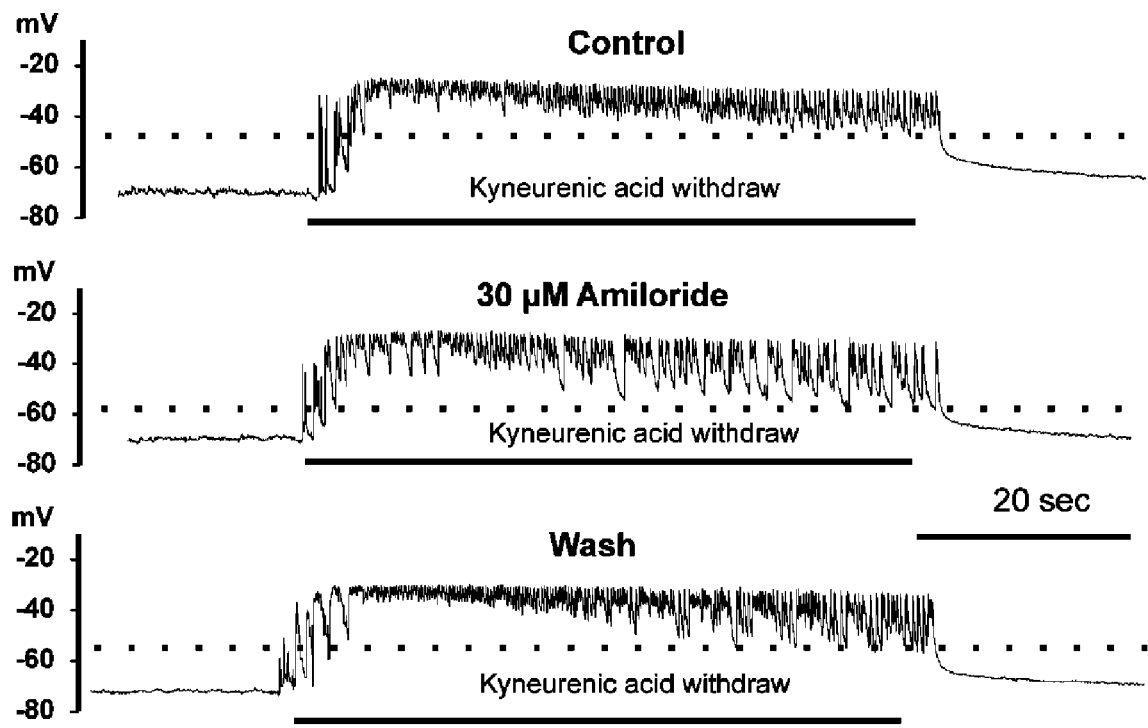
FIGS. 3A-3D are a collection of graphs presenting exemplary electrophysiological data collected by patch-clamp recordings taken from cultured mouse hippocampal neurons exhibiting seizure-like electrical activity in response to removal of kynurenic acid from the culture medium, with the effect of amiloride and PcTX1 venom on the seizure-like electrical activity being tested.
Figure 3B:
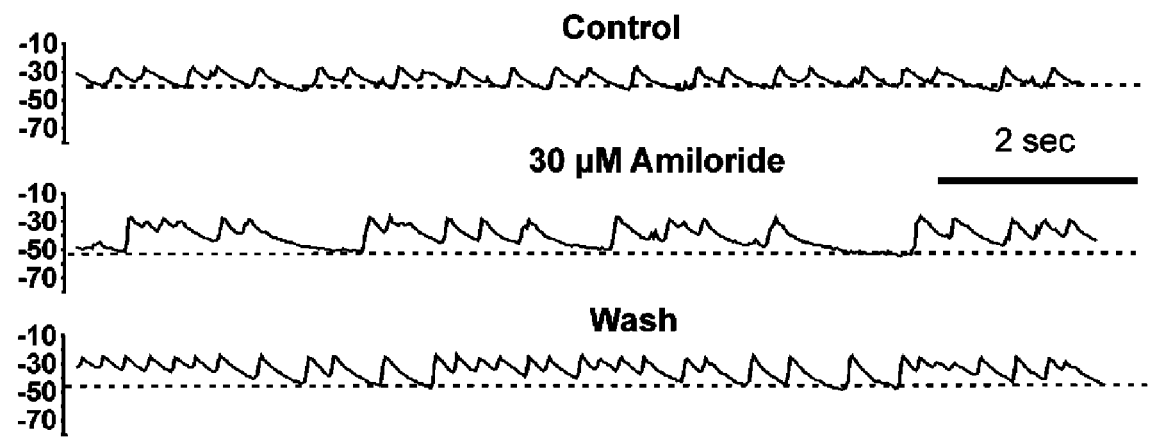
Figure 3C:
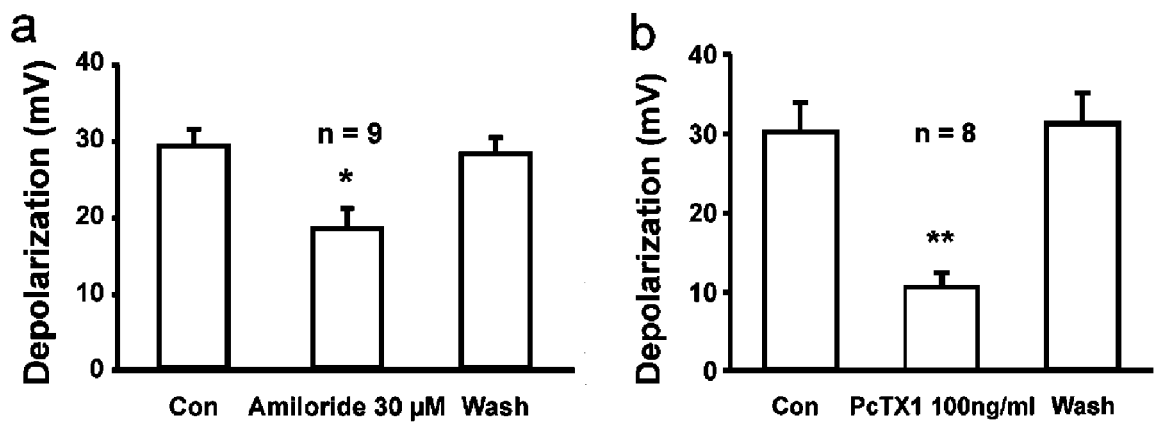
Figure 3D:
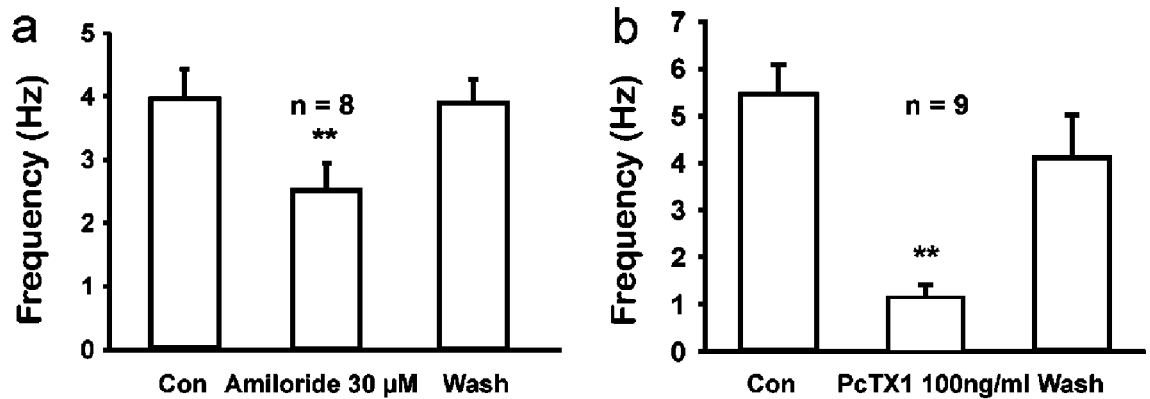

We hypothesized that ASICs are involved in seizure propagation. Using the Furshpan and Potter cell culture model of epilepsy (Meller et al., 2003; Furshpan et al., 1998), we tested ASIC blockade in mouse hippocampal neurons cultured with the glutamate antagonist kynurenate (Kyn) and elevated $Mg^{2+}$. In the presence of Kyn, the majority of hippocampal neurons remained quiescent. However, Kyn withdrawal resulted in Intense seizure-like activity of synchronous bursts of electrical responses resembling paroxysmal depolarization shifts (Furshpan et at., 1989). Some neurons exhibited sustained depolarizations that nearly abolished the resting potential. The ASIC subunit non-specific blocker, amiloride (Waldmann et al., 1997; Xiong et al., 2004), and specific homomeric ASIC1a channel antagonist PcTX1 (Xiong et al. 2004; Escoubas et al., 2000), perfused to cells 2 min before and during Kyn withdrawal resulted in attenuated Kyn withdrawal-induced sustained membrane depolarization and paroxysmal bursts (FIGS. 3A and 3B). Without amiloride, Kyn withdrawal-induced sustained depolarization of 39.5±2.1 mV and paroxysmal bursts at 4.0±0.5 Hz. With 30 μM amiloride, membrane depolarization was reduced to 28.6±2.7 mV ($p<0.05$, n=5) and burst activity reduced to 2.5±0.4 Hz ($p<0.01$, FIGS. 3C and 3D). Similarly, application of PcTX1 reduced membrane depolarization from 30.2±3.7 mV to 10.7±1.8 mV (n=8, $p<0.01$) and burst activity from 5.5±0.6 Hz to 1.2±0.3 Hz (n=9, $p<0.01$, FIGS. 3C, 3D, and 4).

Limbic seizures (Avoli et al., 2002) are modeled by removing $Mg^{2+}$ from artificial cerebral spinal fluid (aCSF) in slices of hippocampal-entorhinal cortex, which triggers interictal-like bursting activity, or spontaneous ictal-like events (Wong et al., 2001; Anderson et al., 1986). In the presence of normal $Mg^{2+}$ (1.5 mM), stimulation of Schaffer collaterals induces single population spike or EPSP in the CA1 region of the hippocampus. As the stimulation intensity increases, the amplitude of EPSP also increased without generating multiple population spikes or bursting activity. Perfusion with $Mg^{2+}$-free aCSF for about 30 min evoked synchronous burst firing with the same stimulation intensity. In about, 30% of the slices, spontaneous clustered bursts developed in the absence of electrical stimulation. Bath perfusion of amiloride or PcTX1 for 10 min reduced the amplitude and frequency of evoked bursting activity (FIGS. 5A and 5B). Amiloride (100 μM) reduced the amplitude of the first and the second population spikes (from 1.2±0.2 mV to 0.5±0.2 mV and 0.6±0.03 mV to 0.2±0.05 mV, respectively (n=9: $p<0.01$, FIGS. 5A and 5B), and the number of population spikes (from 4.7±0.6 to 3.3±0.8, n=9, $p<0.05$)). Similarly, PcTX1 (200 ng/mL) attenuated the amplitude of the population spike (from 2.1±0.3 to 1.6±0.2 mV, n=9, $p<0.05$) and the number of spikes (from 4.2±0.6 to 3.0±0.6, $p<0.05$).

Figure 6B:
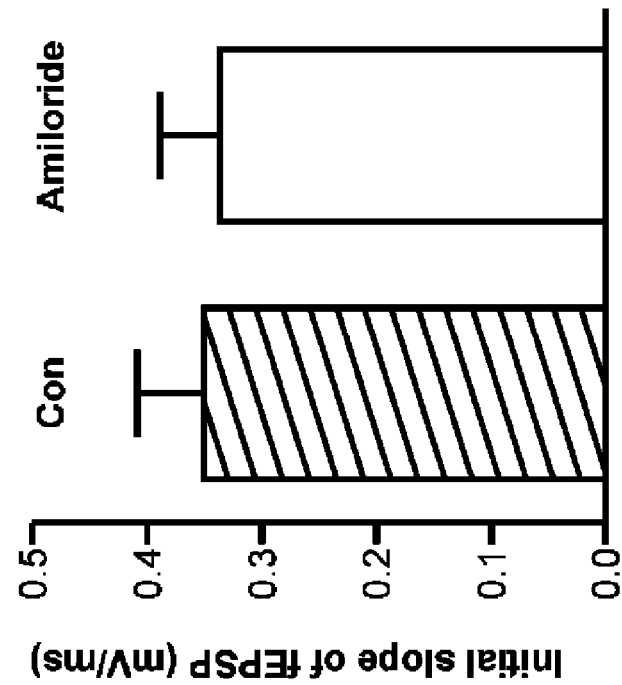
FIGS. 6A and 6B are a set of graphs presenting exemplary electrophysiological data collected using mouse hippocampal slices from which field excitatory postsynaptic potentials (fEPSPs) were measured in the stratum pyramidale and striatum radiatum of the hippocampal CA1 region by stimulating Schaffer collaterals.
Figure 6A:
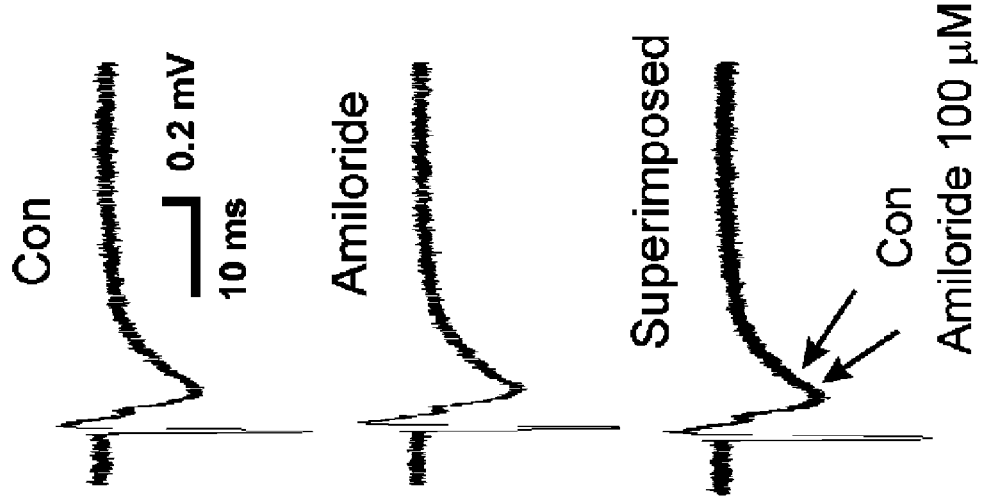

Similar to evoked activity, amiloride reduced spontaneous clustered bursts from 29.8±5.6 $min^{-1}$ to 26.0±5.8 $min^{-1}$ (reduced to 0.84±0.05 of control, n=8, $p<0.05$, FIG. 5C). PcTX1 reduced the frequency from 80.4±11.1 $min^{-1}$ to 59.9±11.3 $min^{-1}$ (reduced to 0.68±0.07 of control, n=9, $p<0.01$, FIG. 5D). Application of amiloride did not affect the amplitude of normal fEPSP in the presence of $Mg^{2+}$ (n=5, FIGS. 6A and 6B), suggesting that activation of ASIC does not play an important role in basal synaptic transmission (Alvarez de la Rosa et al., 2003).

Figure 7E:
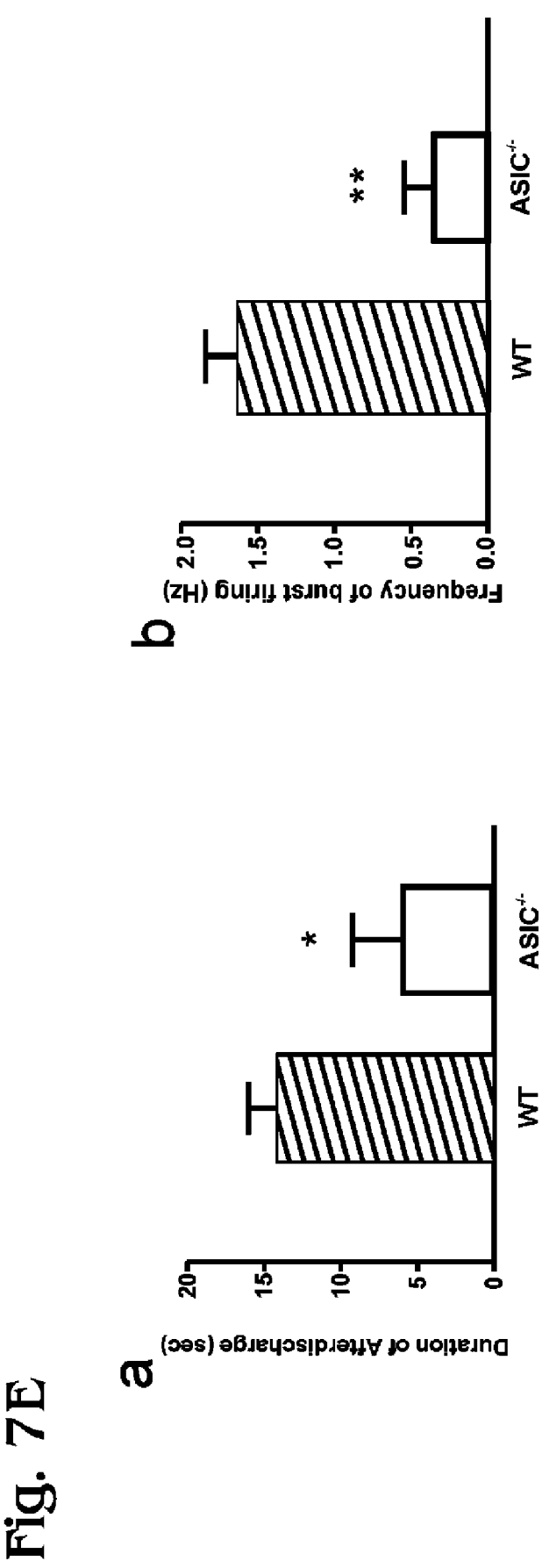

ASIC blockade on seizure-like bursting activity induced by high frequency stimulus trains, e.g., after-discharges (Stasheff et al., 1985), was determined as high frequency electric stimulation generates epileptic bursting without disrupting the balance of excitation versus inhibition thus more closely mimicking epileptogenesis in vivo (Stasheff et al., 1985). Following approximately five trains of stimulation, relatively stable after-discharges were recorded (FIGS. 7A-7E). Amiloride bath perfusion reduced after-discharge duration by about 80% (from 21.0±3.5 sec to 4.7±2.4 sec, n=3; $p<0.05$) and burst firing frequency by about 90% (from 2.8±0.4 Hz to 0.3±0.1 Hz, n=3, $p<0.05$, FIG. 7A). Similarly, PcTX1 reduced after-discharge duration from 29.3±8.5 to 11.5±4.1 sec (reduced to 0.44±0.10 of control, n=4, $p<0.05$) and burst firing frequency from 0.9±0.1 to 0.5±0.2 Hz (reduced to 0.5±0.1 of control, n=4, p<0.05, FIG. 7B). Similar to ASIC1a blockade, seizure activity was attenuated in hippocampal slices from ASIC1$^{-/-}$ mice (Xiong et al., 2004) (FIGS. 7C-7E). In wild-type (WT) mice, five sets of stimulus trains generated bursting activity with a duration of 13.9±2.0 sec and a firing frequency of 1.6±0.2 Hz, whereas in slices from ASIC1$^{-/-}$ mice, identical stimulations generated after-discharges of only 5.8±3.3 sec duration and 0.4±0.2 Hz frequency (n=9 for both groups, p<0.05 for difference in duration and p<0.01 for frequency, FIG. 7E). The resistance of ASIC1$^{-/-}$ slices to seizure induction was further demonstrated in detailed plots of stimulation train-dependent development of after-discharges (FIG. 7D). The increased duration and firing frequency developed significantly slower in ASIC1$^{-/-}$ slices than in WT slices (n=9 for both groups, p<0.01, two-way ANOVA).

To determine whether ASIC blockade affects seizure-induced neuronal injury, we tested the effect of ASIC blockade on low Mg$^{2+}$-induced injury of acute hippocampal slices. 400 μm-thick coronal slices were cut and placed on a Millipore membrane in 6-well plates (2 slices in each well). Slices were randomly divided into three groups treated with the following different solutions (for 2 hr): oxygenated aCSF with normal Mg$^{2+}$; oxygenated aCSF without Mg$^{2+}$; oxygenated aCSF without Mg$^{2+}$ plus 100 μM amiloride. 100 μL medium was collected from each slice 6 hr following the incubation for the measurement of lactate dehydrogenase (LDH). The LDH value was then normalized to the maximal releasable LDH to give % of cell death. With aCSF containing normal Mg$^{2+}$, 6.2±0.9% of maximal LDH release was recorded. In the absence of Mg$^{2+}$, this value was increased to 13.0±2.2%. Addition of aniloride decreased relative LDH release to 6.0±0.4% (n=3). Similar reduction of low Mg$^{2+}$-induced cell death was observed with a propidium iodide (PI) staining technique.

Figure 8A:
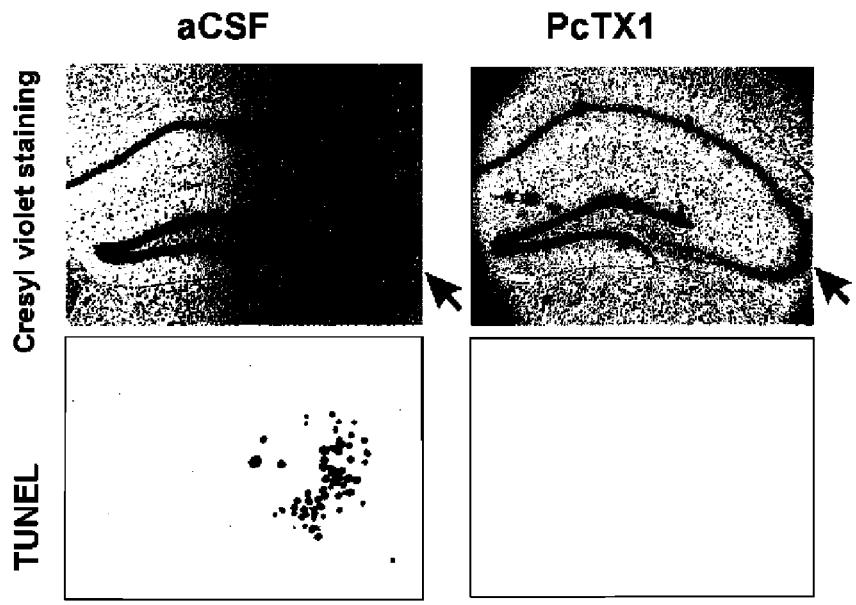
FIGS. 8A-8D are a collection of photographs and graphs presenting exemplary data collected from WT and ASIC1$^{-/-}$ mice treated with kainic acid (KA) to provide an in vivo model of epilepsy.
Figure 8B:
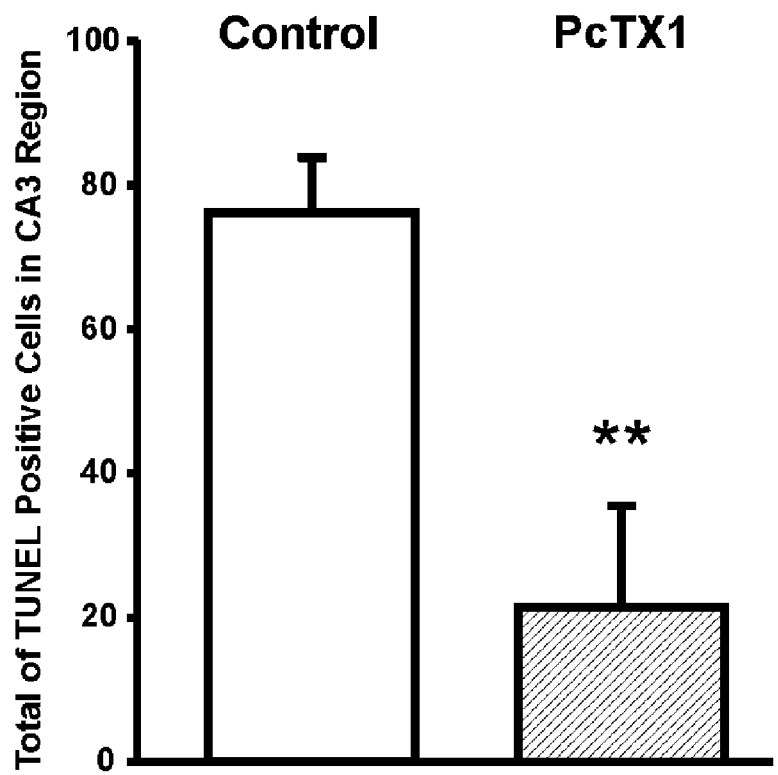
Figure 8C:
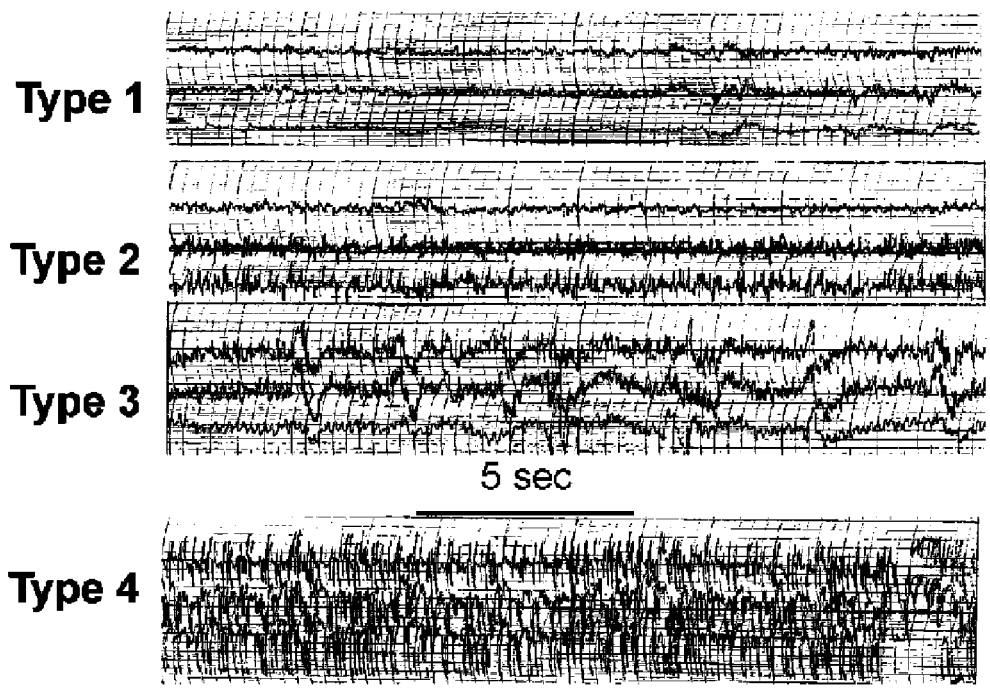
Figure 8D:
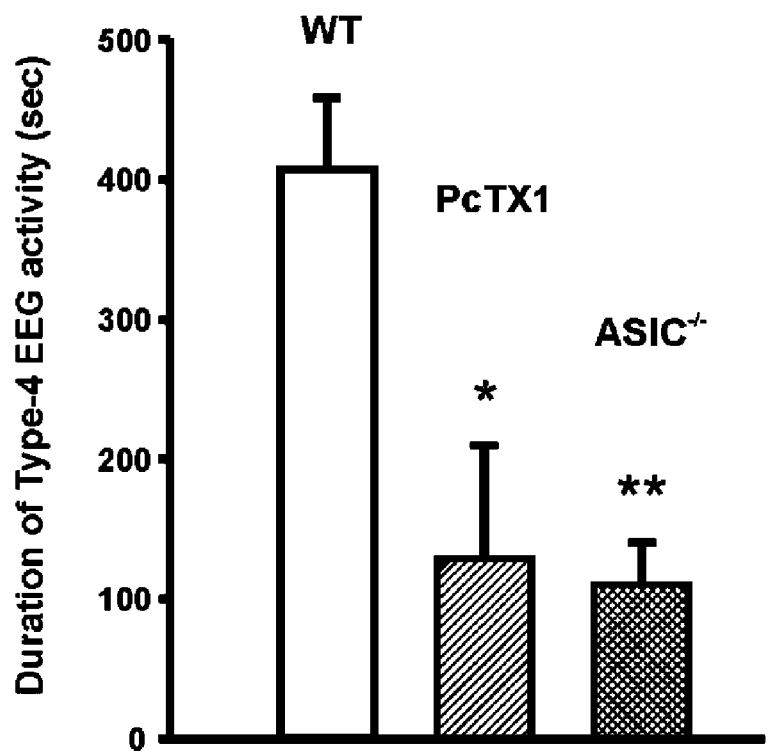

In an in vivo model of epilepsy (Araki et al., 2002), WT and ASIC1$^{-/-}$ C57BL/6 mice. 20-25 g, had unilateral microinjection of kainic acid (KA) into the basolateral amygdala nucleus. Intracerebroventricular injection (Pignataro et al., 2007), of 0.5 μL of aCSF, or aCSF containing PcTX1 (500 ng/mL) 60 min before the induction of seizure activity resulted in all control mice demonstrating prominent polyspike (type-4) EEG activity of 406.7±51.6 sec in 30 min (n=6), but in mice injected with PcTX1 only two out of six showed polyspike EEG activity of 128.3±60.3 sec (n=6, p<0.05, FIGS. 8C and 8D). Further, significant CA3 neuronal injury occurred in six out of six control mice at 24 hr after KA injection (TUNEL positive cells were 76.2±7.6), but in mice injected with PcTX1, only two out of six showed any CA3 injury (average TUNEL positive cells were 21.8±14.1, n=6, p<0.01, FIGS. 8A and 8B). Identical KA injection in ASIC1$^{-/-}$ mice produced attenuated polyspike EEG activity (total duration: 109.8±30.8 sec, n=6, p<0.01 versus WT control, FIG. 8D).

Unlike ischemia, only moderate pH changes (e.g., ~0.3 pH unit) are reported in brain parenchyma during seizures (Chesler et al., 1988: Chesler et al., 1992), although pH in the synaptic cleft may be much lower (Chesler et al., 1992; Wemmie et al., 2006). Such small changes of pH$_o$ have not been shown to activate significant ASIC current in voltage-clamp recordings at normal condition, though biochemical changes associated with seizures (e.g., low [Ca$^{2+}$]$_o$) may dramatically increase the sensitivity of the channels to smaller decreases in pH$_o$. One possibility is that voltage-clamp recording has relatively low sensitivity to resolve small current in whole-cell configuration. To provide more evidence that the decreases of pH$_o$ to the level seen in epilepsy can indeed activate the ASICs and cause neuronal excitation, we have also used current-clamp recording to study changes of membrane depolarization and neuronal firing by small changes of pH$_o$. Due to the large input resistance of most CNS neurons (e.g., ~500 MΩ), even a small membrane current (e.g., 10-20 pA, which is difficult to resolve in voltage-clamp recording in general) can induce significant membrane depolarization in current-clamp conditions. Mouse cortical neurons were used for current-clamp recordings 14 days after the culture. To show that decreases of pH$_o$ reported in epilepsy can cause neuronal excitation through ASICs, we examined changes of membrane potential and neuronal firing by small changes of pH$_o$.

Figure 9A:
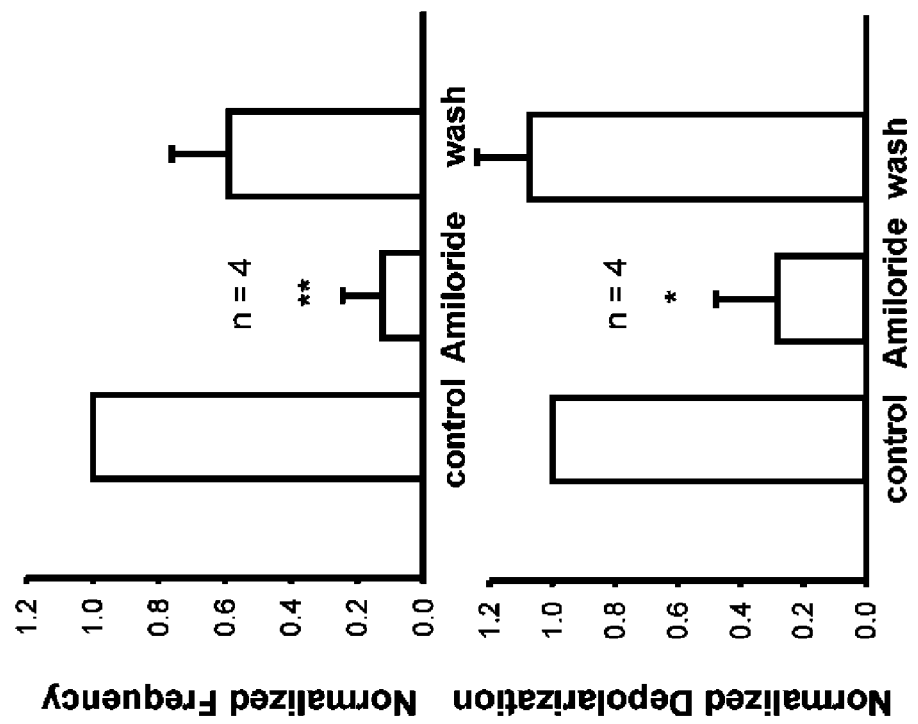

As shown in FIGS. 9A and 9B, perfusion of neurons at pH 7.0 induced approximately 30 mV membrane depolarization and dramatically increased firing rate. Amiloride (100 μM) or synthetic PcTX1 (20 nM) largely and significantly reduced this acid-induced neuronal excitation (n=3-4). Lowering pH to 7.1 also induced a depolarization of approximately 15 mV and increased firing of action potentials, which are sensitive to PcTX1 inhibition, (FIG. 9C). These data support the notion that a mild drop of pH$_o$, as reported during seizure activity, can cause neuronal excitation through activation of ASICs, thus participating in the propagation of epileptic seizures.

Figure 10B:
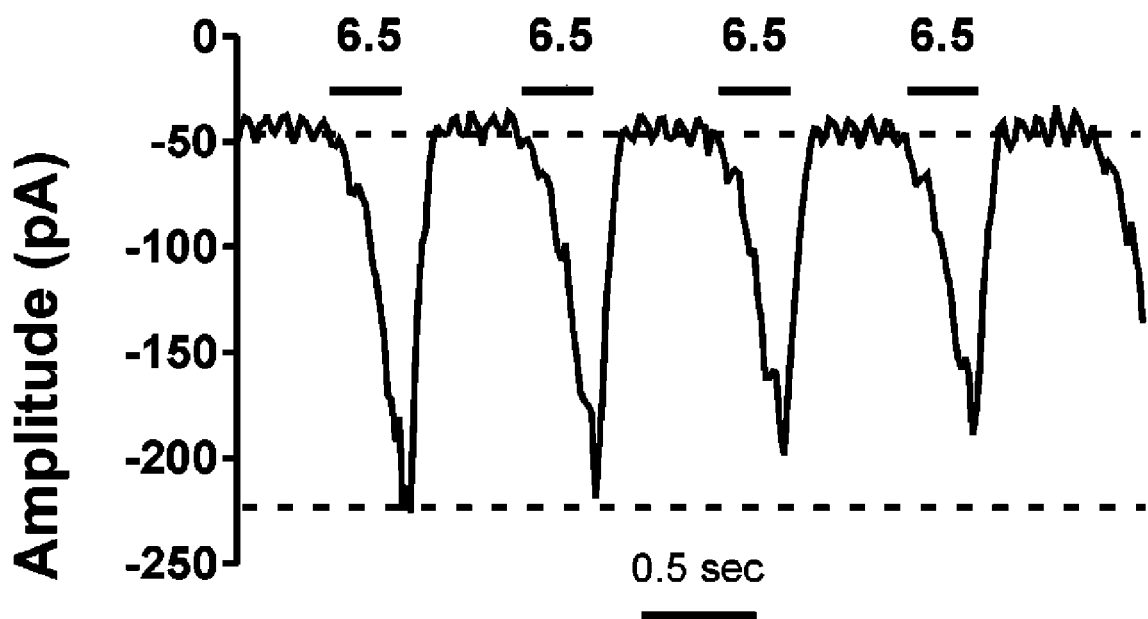

Seizures produce high frequency synchronous firing of neuronal populations. Since synaptic vesicles are highly acidic (pH<5.7) (Miesenbock et al., 1998), release of neurotransmitter is expected to induce high frequency fluctuation of extracellular pH (pH$_o$) at the synaptic cleft (Chesler et al., 1992) where ASIC1a channels are enriched (Zha et al., 2006). Fluctuation of pH$_o$ during seizure activity is expected to activate these channels, facilitating neuronal excitation. However, ASICs undergo desensitization following activation (Hesselager et al., 2004). Thus, the channels need to recover rapidly from desensitization to be activated repeatedly by high frequency acid pulses. We have shown that, one second after a complete desensitization following a prolonged acid pulse, >50% of ASIC current can be re-activated by acid application (Wang et al., 2006). To more closely mimic the condition during seizure activity, where acid pulse is expected to be brief, we recorded ASIC current induced by short (0.3-0.5 second), high frequency repeated acid pulses. Here, ASICs only partially desensitize or no desensitization occurs. Following brief recovery in normal pH (0.5 second), the channel is activated again by the next acid pulse. As shown in FIGS. 10A and 10B, ASIC current can be repeatedly activated for prolonged periods with little attenuation. This finding provides additional evidence that ASICs can play a role during high frequency acid fluctuation expected to occur in seizure activity.

The activity-dependent pH changes are notable for their regional diversity. Although intense neuronal activity in general induces a predominant extracellular acidification in various brain regions, in regions such as cerebellum, cortex, and CA1 and CA3 regions of hippocampus, neuronal activity is accompanied by an initial extracellular alkalinization, followed by acidification. Brief alkalinization may reduce the steady-state inactivation of the ASICs thus increasing the availability of the channels to be activated by a subsequent acid pulse resulting in increased current amplitude.

C. Discussion

Epilepic neuronal excitation induces local acidosis from neurotransmitter release (DeVries, 2001; Krishtal et al., 1987; Miesenbock et al., 1998), induced acid secretion from glial cells (Chesler, 2003), and metabolic production of lactate (Simon, 2006). Although parenchymal pH$_o$ drops of about 0.3 units have been reported during seizures (Chesler et al., 1988; Chester et al., 1992; Urbanics et al., 1978), synaptic cleft pH drops maybe pronounced (Chester et al., 1992; Wemmie et al., 2002). Further, extracellular acid buffer and multiple acid transporters in CNS (Chester, 2003) suggest high frequency pH fluctuation at the synaptic cleft during seizures. ASICs are prominent in brain and pathogenic in ischemia (Benveniste et al., 2005; Huang et al., 2004; Xiong et al., 2004), but their role in acid signaling during seizures was substantially unexplored. We show here that moderate acidosis can induce membrane depolarization and excitation of CNS neurons through ASIC1a activation. Further, a simultaneous reduction of $[Ca^{2+}]_o$ during seizure activity should further facilitate ASIC activation (Immke et al., 2001). We show ASIC1a activation occurs repeatedly by high frequency acid pulses with little attenuation. In cell culture, brain slice, and in vivo models of epilepsy, we demonstrate that ASIC1 blockade and ASIC1 gene knockout attenuate seizure propagation.

Though acidosis has been reported to inhibit the function of some ion channels (DeVries, 2001), an increase in neuronal excitation has been well-demonstrated in peripheral (Steen et al., 1992), and in CNS neurons as shown here. The abundance of ASIC1a in brain, its localization at excitatory postsynaptic sites (Zha et al., 2006), sensitivity to mild acidic pH, and capability of activation repeatedly by high frequency acid pulses, suggest the participation of these channels in the propagation of seizures. The results presented in this Example provide strong evidence supporting this hypothesis.

D. Figure Legends

FIG. 3. ASIC1 blockade inhibits seizure-like burst activity in a cell culture model of epilepsy. A. Representative seizure-like burst activity induced by withdrawal of kynurenic acid (Kyn). Following long-term (about 4 weeks) culture of mouse hippocampal neurons in the presence of Kyn and high $Mg^{2+}$, withdrawal of Kyn induces seizure-like activity consisting of high frequency bursts and synchronous depolarization shifts (Furshpan et al., 1989). Bath application of the non-selective ASIC1 blocker amiloride significantly suppresses the seizure-like activity. B. Extended time-scale showing individual depolarization shifts before and after bath application of 30 μM amiloride. C. Summary data showing reduction in the magnitude of Kyn withdrawal-induced membrane depolarization by amiloride (a; n=8, p<0.05) and PcTX1 (b; n=9, p<0.01). D. Summary data showing reduction in the frequency of Kyn withdrawal-induced synchronous depolarization shifts by amiloride (a; n=8, p<0.01) and PcTX1 (b; n=9, p<0.01).

Figure 4:
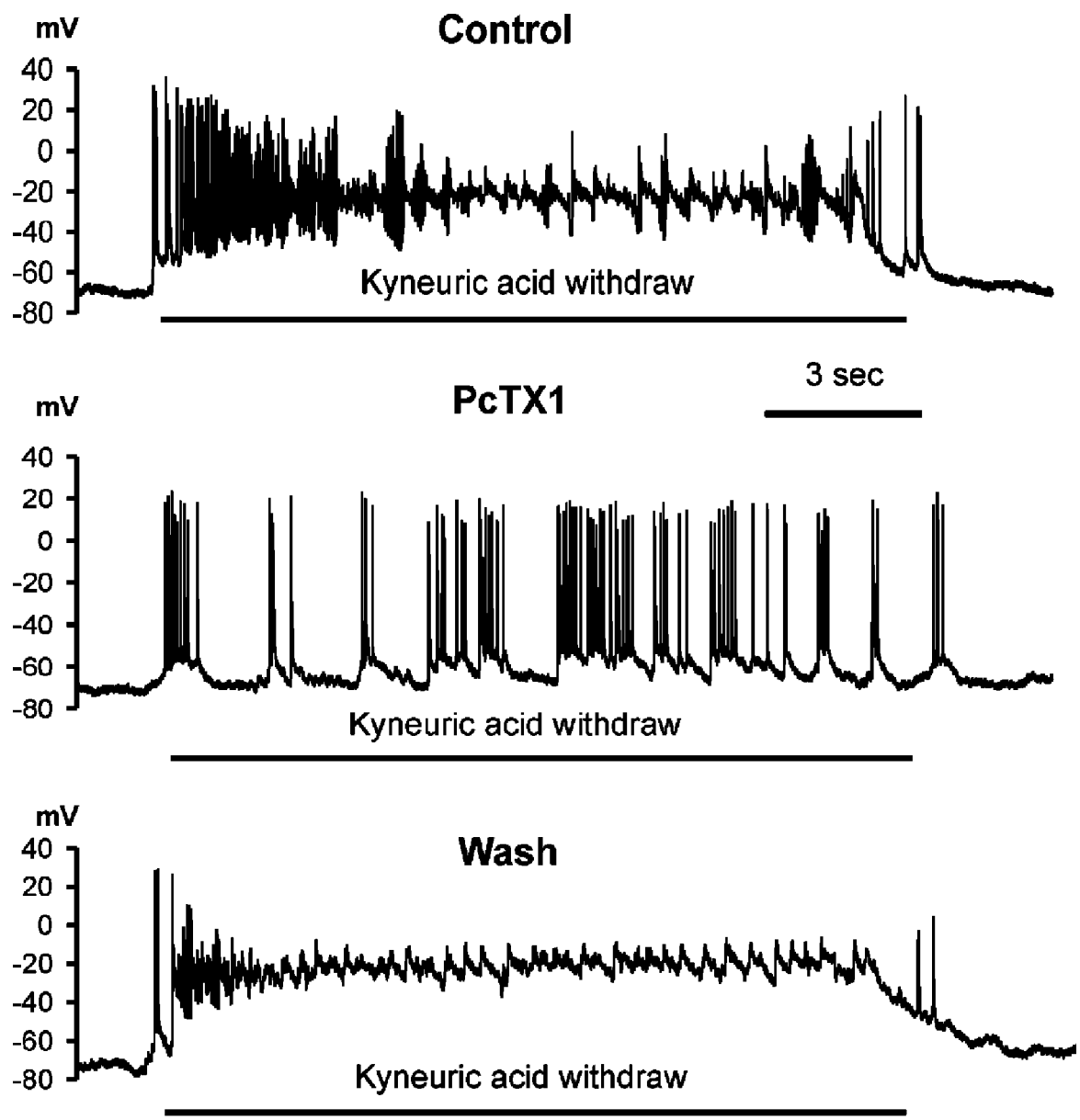
FIG. 4 is a set of graphs presenting exemplary electrophysiological data collected as patch-clamp recordings of cultured mouse hippocampal neurons treated as in FIG. 3 to induce seizure-like electrical activity.

FIG. 4. Representative seizure-like burst activity induced by withdrawal of kynurenic acid (Kyn) in the absence and presence of specific ASIC1a blocker PcTX1 (Xiong et al., 2004). Following long-term (~4 weeks) culture of mouse hippocampal neurons in the presence of Kyn and high $Mg^{2+}$, withdrawal of Kyn induced seizure-like activity consisting of high frequency bursts of synchronous depolarization shifts. Bath perfusion with PcTX1 venom (200 ng/mL total protein) reduced Kyn withdrawal-induced seizure-like synchronous depolarization shifts (see FIGS. 3C and 3D for more detail).

FIG. 5. ASIC1 blockade inhibits seizure-like burst activity in mouse hippocampal slices. A. In the absence of $Mg^{2+}$, single electrical stimulation of a Shaffer collateral pathway can evoke seizure-like busting activity in CA1 region. Bath perfusion of the non-selective ASIC1 blocker amiloride reduces the amplitude and frequency of evoked bursting activity. A-a. Representative population spikes evoked by a single electrical stimulation in the absence and presence of 100 μM amiloride A-b. Summary data showing reduction in the amplitude of the first population spike by amiloride (n=9, **p<0.01). A-c. Summary data showing reduction in total number of population spikes by amiloride (n=9, *p<0.05). B. Bath perfusion with the ASIC1 specific blocker PcTX1 inhibits evoked bursting activity in the absence of $Mg^{2+}$. B-a. Representative population spikes evoked by a single electrical stimulation in the absence and presence of 200 ng/mL PcTX1 venom. B-b. Summary data showing reduction in the amplitude of the first population spike by PcTX1 (n=9, *p<0.05). B-c. Summary data showing reduction in the total number of population spikes by PcTX1 (n=9). C. Effect of amiloride on spontaneous clustered bursting activity in the absence of $Mg^{2+}$. Bath perfusion with amiloride reduced the frequency of spontaneous clustered bursting activity (n=8, *p<0.05). D. Effect of PcTX1 on spontaneous bursting activity in the absence of $Mg^{2+}$. Bath perfusion with 200 ng/mL PcTX1 venom or 20 nM synthetic PcTX1 reduced the frequency of the spontaneous clustered bursting activity (n=9, p<0.01).

FIG. 6. Representative field-EPSPs and summary data showing the lack of inhibition by amiloride on basal synaptic transmission. In the presence of $Mg^{2+}$ (1.0 mM), stimulation of Schaffer collaterals induced field excitatory postsynaptic potential (fEPSP) in the CA1 region of the hippocampus. Application of amiloride (100 μM) did not affect the amplitude or slope of the field-EPSP in the presence of $Mg^{2+}$ (n=5), suggesting that activation of ASIC does not modify basal synaptic transmission (Alvarez de la Rosa, 2003).

FIG. 7. ASIC blockade or ASIC1 gene knockout suppresses stimulus train induced after-discharges. A-a. Representative after-discharges induced by stimulus trains in the absence and presence of amiloride. A-b, A-c. Summary data showing reduction in the duration of after-discharges and the frequency of burst firing by 100 μM amiloride (n=3, *p<0.05). B-a. Representative after-discharges induced by stimulus trains in the absence and presence of 200 ng/mL PcTX1. B-b, B-c. Summary data showing reduction in the duration of after-discharges and the frequency of burst firing by PcTX1 (n=4, *p<0.05). C. Representative after-discharges induced by $5^{th}$ or $10^{th}$ stimulus trains in slices from WT (upper panels) or ASIC1$^{-/-}$ mice (lower panels). D. Summary data showing a stimulus train-dependent increase in the duration of after-discharges and the frequency of burst firing in slices from WT (■) or ASIC1$^{-/-}$ (○) mice (n=9 slices in each group, p<0.05 between WT and ASIC1$^{-/-}$ mice for duration and frequency, two-way ANOVA). E. Summary data showing the duration of after-discharges and the frequency of the burst firing induced by $5^{th}$ stimulus trains in WT and ASIC1$^{-/-}$ mice (n=9 in each group, *p<0.05, **p<0.01 compared with WT control group).

FIG. 8. ASIC1 blockade or ASIC1 gene knockout inhibits epileptic seizure activity and seizure-induced CA3 neuronal injury in an in vivo model of epilepsy. A. Representative brain sections showing image of hippocampus CA3 neuronal injury in aCSF-injected but not in PcTX1-injected mice 24 hr following KA injection. Lower panels represent enlarged CA3 region showing TUNEL-positive staining (i.e., cell death) in mice injected with aCSF but not PcTX1. (TUNEL-positive cells are visible in this inverted image as black dots.) B. Summary data showing the total number of TUNEL positive cells in CA3 region of hippocampus from mice injected with aCSF or PcTX1 (n=6 in each group, **p<0.01). C. Representative EEG recording showing different types of brain activity. Type 1-baseline; Types 2 and 3-ictal onset; Type 4-polyspike paroxysmal burst. D. Summary data showing total duration of polyspike paroxysmal burst activity (Type 4) within 30 min after KA injection in WT mice, ASIC1$^{-/-}$ mice, and in WT mice injected with PcTX1 (n=6 in each group, *p<0.05, **p<0.01).

Figure 9A:
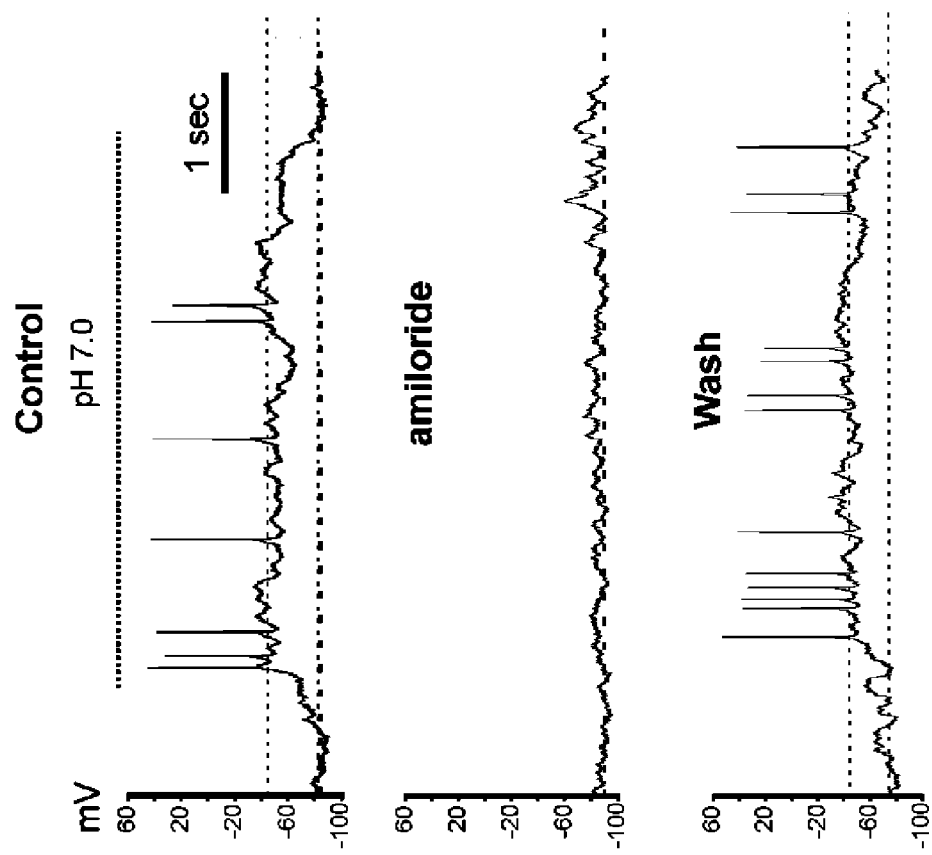
Figure 9C:
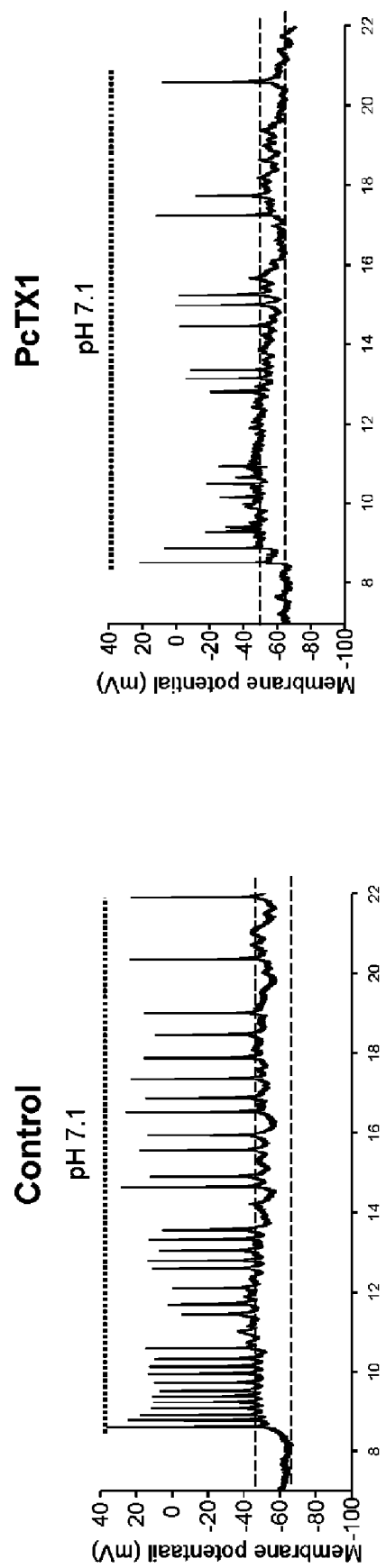

FIG. 9. Moderate pH drops reported during seizure activity can cause neuronal excitation through ASIC1a activation. A. Representative raw data and summary graphs showing reduction of acid pH 7.0)-induced membrane depolarization and increased firing of action potentials in mouse hippocampal neurons by 100 μM amiloride (n=4 *p<0.05, **p<0.01). B. Representative raw data and summary graphs showing reduction of acid (pH 7.0)-induced membrane depolarization and increased neuronal firing of action potentials by 20 nM synthetic PcTX1 (n=3, *p<0.05). C. Representative current-clamp recording showing reduction of acid (pH 7.1)-induced membrane depolarization and increased neuronal firing by PcTX1.

FIG. 10. Evidence that ASIC1a channels can be repeatedly activated by high frequency acid pulses. A. Representative current traces showing ASIC1a current activated by repeated acid pulses (pH 6.5) at different membrane potentials as indicated. The duration of acid pulse is 0.5 sec. The time between the end of the first acid pulse and the beginning of the next acid pulse is 0.5 sec. The same findings were recorded in five cells. B. Representative current traces showing ASIC1a current activated by repeated acid pulses of 0.3 second in duration, spaced by 0.5 second intervals.

E. Methods

Cell culture model of epilepsy. Long term cell culture model of epilepsy was performed as described (Furshpan et al., 1989; Meller et al., 2003). Briefly, hippocampal neurons prepared from 1-2 day-old C57BL/6 mice cultured in Neurobasal-A/B27 media supplemented with 10 mM Kyn and 5 mM MgCl$_2$. Culture media was replenished with fresh kynurenic acid/Mg$^{2+}$ every 3 days. Cells were used for patch-clamp recording after 3 to 4 weeks. Following the formation of a tight seal in a whole-cell configuration, neurons were current-clamped at ~–60 mV. In the presence of Kyn, the majority of hippocampal neurons remained quiescent. Upon washout of Kyn, almost all neurons displayed seizure-like activity consisting of bursts of synchronous electrical responses that resembled paroxysmal depolarization shifts (Furshpan et al. 1989). The spontaneous electrical behavior of the culture has many of the characteristics of seizure activity in an intact cortex. This system allows seizure-related cellular mechanisms to be studied in long-term cell culture.

Cortical neuronal culture. Primary neuronal cultures were prepared from embryonic Swiss mice at 15 to 16 days of gestation according to our previously described techniques (Xiong et al., 2004). In brief, cerebral cortices from 10 to 12 embryos were dissected and incubated with 0.05% trypsin-EDTA for 10 min, dissociated by trituration with a fire-polished glass pipette, and plated on poly-L-ornithine-coated culture dishes at a density of 0.5×10$^6$ cells per dish. Neurons were cultured with Neurobasal medium supplemented with B27 (Invitrogen). The cultures were maintained at 37° C. in a humidified 5% CO$_2$ atmosphere incubator and were used for experiments after 12-14 days.

Patch clamp techniques. Whole-cell voltage-clamp and current-clamp recordings were performed as described in our previous studies (Xiong et al., 2004). Patch electrodes were constructed from thin-welled borosilicate glass (1.5 mm diameter, WPI, Sarasota, Fla., USA) on a two-stage puller (PP83 Narishige, Tokyo). The resistances of patch electrodes were 1.5-3 MΩ when filled with the intracellular solution (see below). Whole-cell currents were recorded using Axopatch 200B amplifiers with pCLAMP software (Axon Instruments, CA, USA). Data were filtered at 2 kHz and digitized at 5 kHz using Digidata 1322 (Axon Instruments). During each experiment, a voltage step of –10 mV was applied periodically to monitor the cell capacitance and the access resistance. A multi-barrel perfusion system (SF-77, Warner Instrument Co., Conn., USA) was employed to achieve a rapid exchange of solutions. All experiments were performed at room temperature (22-24° C.).

Preparation of hippocampal slices and brain slice recording. Hippocampal slices were obtained from 8- to 10-week-old mice. The protocol for brain-slice recording was approved by the Institutional Animal Care and Use Committee of Legacy Research. Animals were deeply anesthetized with isoflurane and decapitated. Brains were quickly removed and placed in ice-cold solution that contained: 125 mM sucrose, 2.5 mM KCl, 26 mM NaHCO$_3$, 1.25 mM NaHPO$_4$, 6.0 mM MgSO$_2$, 0.5 mM CaCl$_2$, and 10 mM glucose, and was saturated with 95% O$_2$ and 5% CO$_2$ (pH 7.4). Hippocamnpal slices were cut in 400 μm thickness in transverse plane with a vibratome (Leica VT 1000S) and placed in a slice holding chamber (BSC-PC Prechamber, Warner Instrument) and incubated in normal artificial cerebral spinal fluid (aCSF) that contained: 125 mM NaCl, 2.5 mM KCl, 26 mM NaHCO$_3$, 1.25 mM NaHPO$_2$, 1.0 mM MgSO$_4$, 2.0 mM CaCl$_2$, and 10 mM glucose, and was saturated with 95% O$_2$ and 5% CO$_2$ (pH 7.4).

Following ~60 min of incubation at room temperature, individual slices were transferred to a submerged slice chamber with a volume of 0.5 mL (Warner Instruments, Hamden, Conn.) and perfused with oxygenated aCSF (35° C.) at a rate of 3-4 mL/min. Recording electrodes were pulled from borosilicate glass and filled with aCSF. The population spike and the field excitatory postsynaptic potentials (fEPSP) were recorded in stratum pyramidale and striatum radiatum of hippocampal CA1 region, by stimulating Schaffer Collaterals.

For low Mg$^{2+}$ induced epileptic burst activity, Mg$^{2+}$-free aCSF was perfused to the slices for ~30 min. For stimulus-train induced bursting discharges (STIB), each stimulation train consisted of 120 pulses at 60 Hz and each pulse was 100 μsec in duration (Stasheff et al., 1985). A 10-minute interval of non-stimulation was provided between successive trains of high frequency stimulation. Stimulation electrodes were located in striatum radiatum between CA1 and CA3 region. The population spikes were recorded from striatum pyramidale of the CA3 region.

Different from the low Mg$^{2+}$ model which promotes excitatory synaptic transmission, the stimulus trains generate epileptic bursting by repetitive and strong electrical stimulations without disrupting the system from the balanced neuronal circuits (excitation vs. inhibition). Compared with pharmacological (e.g., picrotoxin) and ionic (e.g., low Mg$^{2+}$) models, electrical stimulation models may more closely mimic epileptogenesis in vivo.

TUNEL staining. Following cryostat sectioning, slices were air-dried, fixed in 10% formalin for 15 min, washed three times in PBS, permeabilized in 3% Triton X-100 for 20 min, and washed three times in PBS. Slices were subsequently incubated with a reaction mixture that contained FITC-dUTP and 300 U/mL terminal deoxy-transferase (TdT) for 90 min at 37° C. Cultures were then viewed with a fluorescent microscope at an excitation/emission wavelength of 500/550 nm (green) for FITC-TUNEL labeled cells.

Intracerebroventricular injection in mice. The procedure was performed as described in our previous studies (Pignataro et al., 2007; Xiong et al., 2004). A burr hole was drilled through the skull and a cannula inserted in the right lateral ventricle. The cannula was inserted stereotactically at 0.5 mm posterior, 1.0 mm lateral, and 3.0 mm ventral to the bregma, 0.5 µL of aCSF, amiloride, or PcTX1 was infused 60 min before KA injection.

In vivo KA-induced seizure model. A KA-induced in vivo seizure model was implemented as described in our previous studies (Araki et al., 2002). The protocol for seizure-induction in vivo in mice was approved by the Institutional Animal Care and Use Committee of Legacy Research. Adult male wild-type and ASIC1$^{-/-}$ mice with genomic background of C57BL/6, 20-25 g in weight, were used for seizure induction by unilateral microinjection of KA into the basolateral amygdala nucleus based on stereotactic coordinates (AP −0.94 mm, L −2.85 mm, and V −3.75 mm relative to the Bregma). After anesthesia and catheterization of the femoral vein, animals were placed in a stereotactic frame modified with a headpiece compatible for the mouse (Kopf Instruments) and kept under anesthesia using a mixture of 68.5% $N_2O$, 30% $O_2$, and 1.5% isoflurane. Rectal body temperature was kept at 37±1° C. during and after the operation using either a heating pad or heating lamp (Harvard Instruments, Holiiston, Mass.). Using dental cement (Plastics One, Inc.), three skull-mounted recording electrodes were affixed to mice (Plastics One, Inc., Roanoke, Va.) and a 26-gauge steel guide cannula over the intact dura. Anesthesia was discontinued, EEG recordings commenced, and seizures were induced by injection of 0.3 µg KA in 0.2 µL PBS (pH 7.4) into the amygdala via a 31-gauge internal cannula inserted into the lumen of the guide canula. The EEG was monitored for 30 min using a Grass Electroencephalogram (Model 8-16), and lorazepam (6 mg/kg, i.p.) Was then administered to terminate seizures. The EEG was further monitored for up to 30 min to ensure seizure cessation. The duration of polyspike (type 4) EEG activity for each mouse was calculated blind offline. Twenty-four hours following KA injection, mice were killed and brains were immediately frozen in 2-methyl butane (−30° C.) and sectioned at 12 µm on a cryostat. Coronal sections at the level of Bregma −1.7 mm were air dried (15 min), postfixed in 10% formalin (10 min), washed twice in PBS, and then processed for histopathology (cresyl violet staining) (Araki et al., 2002).

Calcium inagong. Briefly, cultured neurons were incubated in Fura-2-acetoxymethyl ester (5 µM) for 40-50 min followed by washing 3 times with dye-free solution. Coverslips with Fura-2 loaded cells were transferred to a perfusion chamber on an inverted microscope (Nikon). Cells were illuminated using a xenon lamp (75 W) and observed using a 40× UV fluor oil-immersion objective lens (Nikon). Video images were obtained using a cooled CCD camera (Sensys KAF 1401, Photometrics). Digitized images were acquired using a PC-type computer controlled by Axon Imaging Workbench software (AIW2.1. Axon Instruments). The shutter and filter wheel (Lambda 10-2) were also controlled by AIW to allow illumination of cells at either 340 nm or 380 nm excitation wavelengths. Imaging was detected at an emission wavelength of 510 nm. 340/380 nm ratio images were analyzed by averaging pixel ratio values in circumscribed regions of cells in the field of view.

Organotypic brain slice culture. Organotypic brain slices from postnatal C57BL/6, ASIC1a and ASIC2a knockout mice were cultured using an interface method. Whole brains from 10 day-old mice were removed after being anesthetized with halothane. The brains were rapidly removed from the skull and placed in sterile, ice-cold dissecting medium (50% MEM, 50% Hanks BSS, 20 mM Hepes, 6.5 mg/mL glucose, pH 7.15, 10 units/mL penicillirn, and 10 µg/mL streprtonmycin). The brains were then placed on the stage of a vibratome (Leica VT 1000), and sectioned coronally at 400 microns and floated into dissecting media. With the aid of a sterile red sable brush (Ted Pella, Inc. Redding, Calif.), slices were transferred to Millicell culture plate inserts with microporous membranes (pore size 0.4 µm, PICM0R50, Millipore, Bedford, Mass.). The inserts were then placed in a 6-well dish containing culture medium (50% MEM with Hanks salts and L-glutamine, 25% Hanks BSS, 25% horse serum, 20 mM Hepes, 6.5 mg/mL glucose, 10 units/mL penicillin and 10 µg/mL streptomycin, pH 7.2). The slices were maintained in a regular incubator at 37° C. with a 15% $CO_2$ enriched atmosphere. The medium was changed twice a week. Seizure experiments were performed on the slices at 7-10 days in culture.

LDH Assay. Lactate dehydrogenase (LDH) is a stable cytoplasmic enzyme present in all cells. It is rapidly released into the cell culture supernatant upon damage of the plasma membrane and the concentration of LDH released is proportional to the number of cells damaged. Therefore, LDH measurement has been commonly used for cell injury studies. LDH assays were performed using the Cytotoxicity Detection Kit (Cat#1644793, Roche Molecular Biochemicals) and a spectrophotometric mutiwell plate reader (SPECTRAmax, Molecular Devices). Samples (100 µL) of cell culture or brain slice medium were collected in a 96-well plate(s) and mixed with the reaction solution (100 µL) from the kit. Absorbance at $OD_{490}$ nm was measured 30 min after the reaction. Absorbance at a reference wavelength ($OD_{620}$ nm) was subtracted from the measurement.

Pharmacological and electrical bursting models. To induce epileptic burst discharges, $Mg^{2+}$-free aCSF was applied. $Mg^{2+}$-free aCSF was obtained by simply omitting $MgSO_4$ from aCSF.

F. References

The following references are cited in the preceding subsections of Example 1 and are incorporated herein by reference Alvarez de la Rosa, D., Krueger S. R., Kolar A., Shao D., Fitzsimonds R. M., Canessa C. M. Distribution, subcellular localization and ontogeny of ASIC1 in the mammalian central nervous system. *J. Physiol.* 546, 77-87 (2003).

Anderson, W. W., Lewis, D. V., Swartzwelder, H. S., and Wilson, W. A. Magnesium-free medium activates seizure-like events in the rat hippocampal slice, *Brain Res.* 398, 215-219 (1986).

Araki, T., Simon, R. P., Taki, W., Lan, J. Q., and Henshall, D. C. Characterization of neuronal death induced by focally evoked limbic seizures in the C57BL/6 mouse. *J. Neurosci. Res.* 69, 614-621 (2002).

Avoli, M., D'Antuono, M., Louvel, J., Kohling, R., Biagini, G., Pumain R., D'Arcangelo G., and Tancredi, V. Network and pharmacological mechanisms leading to epileptiform synchronization in the limbic system in vitro. *Prog. Neurobiol.* 68, 167-207 (2002).

Benveniste, M., and Dingledine, R. Limiting stroke-induced damage by targeting an acid channel. *N. Engl. J. Med.* 352. 85-86 (2005).

Chesler, M., and Chan, C. Y. Stimulus-induced extracellular pH transients in the in vitro turtle cerebellum. *Neuroscience.* 27, 941-948 (1988).

Chesler, M., and Kaila, K. Modulation of pH by neuronal activity. *Trends. Neurosci* 15, 396-402 (1992).

Chesler, M. Regulation and modulation of pH in the brain. *Physiol Rev.* 83, 1183-1221 (2003).

DeVries, S. H. Exocytosed protons feedback to suppress the $Ca^{2+}$ current in mammalian cone photoreceptors. *Neuron.* 32, 1107-1117 (2001).

Escoubas, P., De Weille, J. R., Lecoq, A., Diochot, S., Waldmann, R., Champigny, G., Moinier, D., Ménez, A., Lazduriski, M. Isolation of a tarantula toxin specific for a class of proton-gated $Na^+$ channels. *J. Biol. Chem.* 275, 25116-25121 (2000).

Furshpan, E. J., and Potter, D. D. Seizure-like activity and cellular damage in rat hippocampal neurons in cell culture. *Neuron*. 3, 199-207 (1989).

Hesselager, M., Timmermann, D. B., and Ahring, P. K. pH Dependency and desensitization kinetics of heterologously expressed combinations of acid-sensing ion channel subunits. *J. Biol. Chem.* 2 79, 11006-11015 (2004).

Huang, Y., and McNamara. J. O. Ischemic stroke: "acidotoxicity" is a perpetrator. *Cell* 118, 665-666 (2004).

Immke, D. C., and McCleskey, E. W. Lactate enhances the acid-sensing $Na^+$ channel on ischemia-sensing neurons. *Nat. Neurosci* 4, 869-870 (2001).

Krishtal, O. A., Osipchuk, Y. V., Shelest, T. N., and Smirnoff, S. V. Rapid extracellular pH transients related to synaptic transmission in rat hippocampal slices. *Brain Res.* 436, 352-356 (1987).

McNamara, J. O., Huang, Y. Z., and Leonard, A. S. Molecular signaling mechanisms underlying epileptogenesis. *Sci. STKE*. 2006. re12 (2006).

Meldrum, B. S., and Rogawski, M. A. Molecular targets for antiepileptic drug development. *Neurother,* 4, 18-61 (2007).

Meller. R, Schindler, C. K., Chu, X. P., Xiong, Z. G., Cameron, J. A., Simon, R. P., and Henshall, D. C. Seizure-like activity leads to the release of BAD from 14-3-3 protein and cell death in hippocampal neurons in vitro. *Cell Death Differ* 10, 539-547 (2003)

Miesenbock, G., De Angelis, D. A., and Rothman, J. E. Visualizing secretion and synaptic transmission with pH-sensitive green fluorescent proteins. *Nature*. 394, 192-195 (1998).

Pignataro, G., Simon, R. P., and Xiong, Z. G. Prolonged activation of ASIC1a and the time window for neuroprotection in cerebral ischaemia. *Brain.* 130, 151-158 (2007), Pitkanen, A., and Halonen, T. Prevention of epilepsy. *Trends Pharmacol. Sci.* 19, 253-255 (1998).

Siesjo, B. K., and Wieloch, T. Epileptic brain damage: pathophysiology and neurochemical pathology. *Adv. Neurol.* 44, 813-847 (1986).

Siesjo, B. K., Katsura, K. and Kristian, T. Acidosis-related damage. *Adv. Neurol.* 71, 209-233 (1996).

Simon, R. P. Status epilepticus mechanisms and management. Wasterlain, C. G., and Treiman, D. M. (eds.): pp. 149-162 (The MIT Press, 2006).

Stasheff, S. F., Bragdon. A. C., and Wilson, W. A. Induction of epileptiform activity in hippocampal slices by trains of electrical stimuli. *Brain Res.* 344, 296-302 (1985).

Steen, K. H., Reeh, P. W., Anton, F., and Handwerker, H. O. Protons selectively induce lasting excitation and sensitization to mechanical stimulation of nociceptors in rat skin, in vitro, *J. Neurosci.* 12, 86-95 (1992).

Urbanics, R., Leniger-Follert, E., and Lübbers. D. W. Time course of changes of extracellular $H^+$ and $K^+$ activities during and after direct electrical stimulation of the brain cortex. *Pflugers Arch.* 378, 47-53 (1978).

Waldmann, R., Champigny, G., Bassilana, F., Heurteaux, C. and Lazdunski, M. A proton-gated cation channel involved in acid-sensing. *Nature* 386, 173-177 (1997).

Wang, W. Z., Chu, X. P., Li, M. H., Seeds, J., Simon, R. P., Xiong, Z. G. Modulation of acid-sensing ion channel currents, acid-induced increase of intracellular $Ca^{2+}$, and acidosis-mediated neuronal injury by intracellular pH. *J. Biol. Chem.* 281, 29369-29378 (2006).

Wemmie, J. A, et al. The acid-activated ion channel ASIC contributes to synaptic plasticity, learning, and memory. *Neuron.* 34, 463-477 (2002).

Wemmie, J. A., Price, M. P., and Welsh, M. J. Acid-sensing ion channels: advances, questions and therapeutic opportunities. *Trends Neurosci.* 29, 578-586 (2006).

Wong, M., and Yamada, K. A. Developmental characteristics of epileptiform activity in immature rat neocortex: a comparison of four in vitro seizure models. *Brain Res. Dev. Brain Res.* 128, 113-120 (2001).

Xiong, Z. G., Zhu, X. M., Chu, X. P., Minami, M., Hey, J., Wei, W. L., MacDonald, J. F., Wemmie, J. A., Price, M. P., Welsh, M. J., and Simon R. P. Neuroprotection in ischemia: blocking calcium-permeable acid-sensing ion channels. *Cell* 118, 687-698 (2004).

Zha, X. M., Wemmie, J. A., Green, S. H., and Welsh, M. J. Acid-sensing ion channel 1a is a postsynaptic proton receptor that affects the density of dendritic spines. *Proc. Natl. Acad. Sci. U.S.A.* 103, 16556-16561 (2006).

Example 2

Amiloride Derivatives as ASIC Inhibitors

Figure 11:
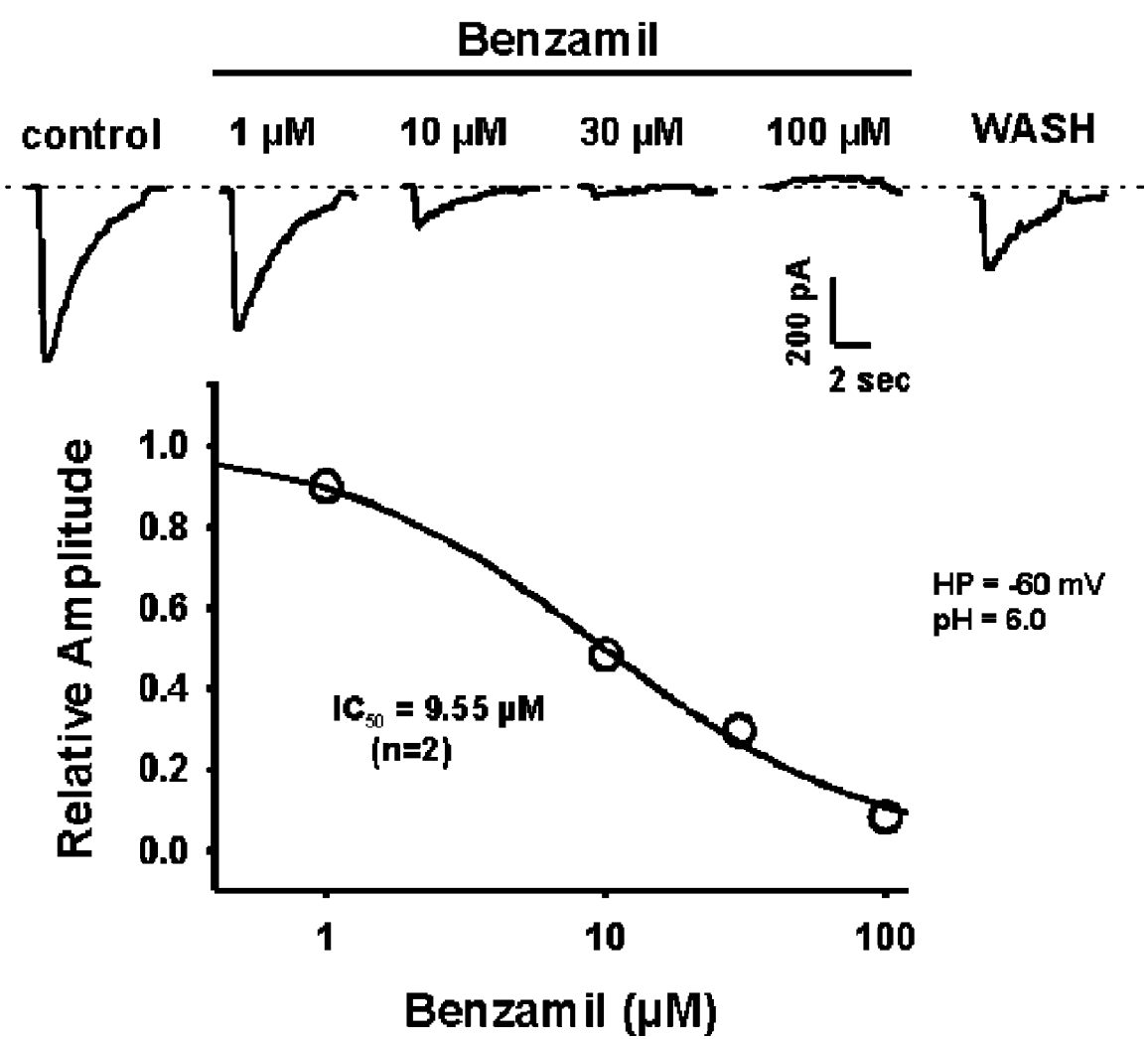
FIG. 11 is a collection of graphs presenting electrophysiological data collected by patch-clamp recording from mouse cortical neurons shifted to a reduced extracellular pH (pH 6.0), to induce an acid-responsive current, in the presence of various concentrations of the amiloride derivative benzamil.
Figure 12:
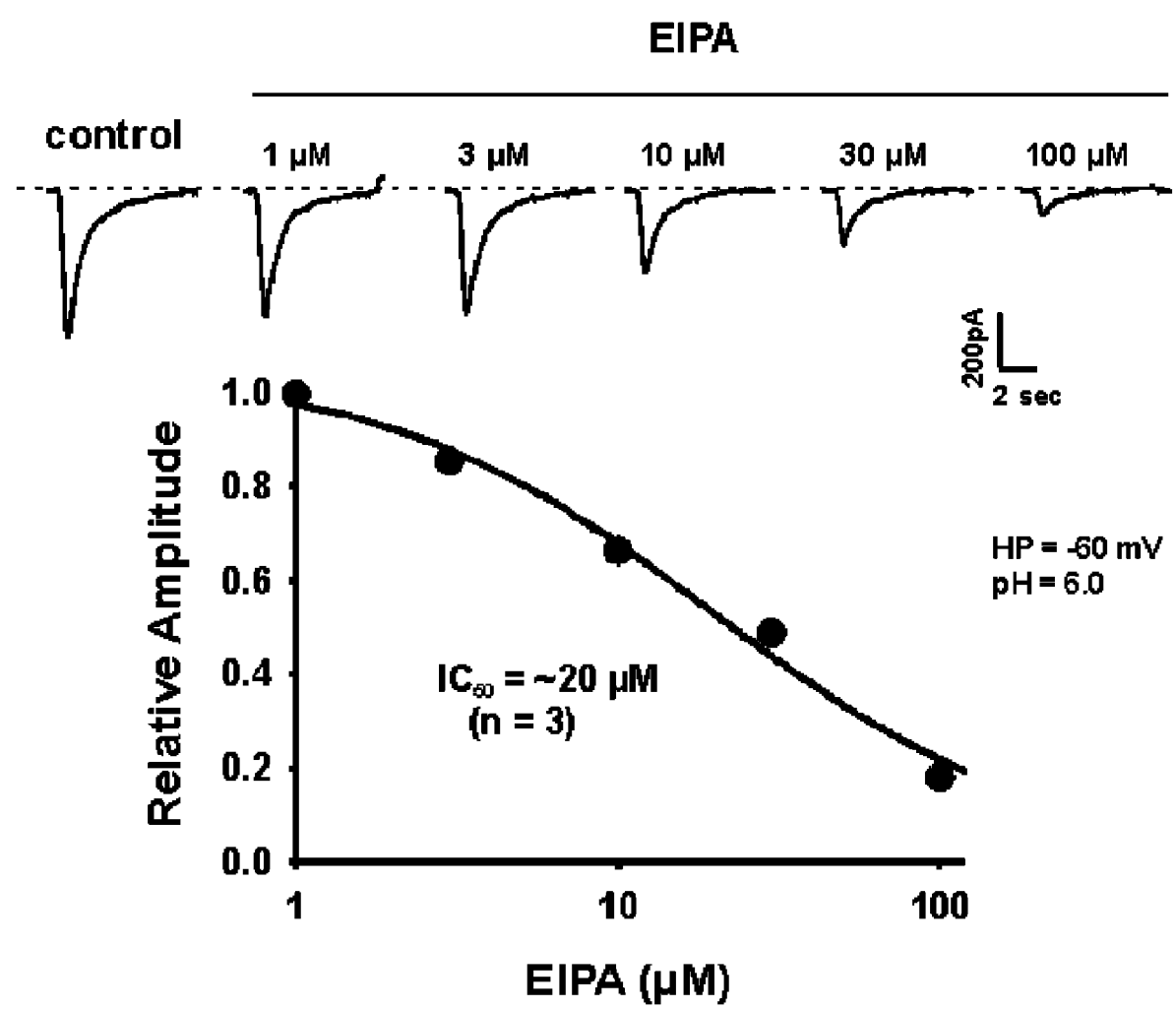
FIG. 12 is a collection of graphs presenting exemplary electrophysiological data collected as in FIG. 11 but in the presence of various concentrations of the amiloride derivative 5-(N-ethyl-N-isopropyl)-amiloride (EIPA).

This example describes patch-clamp experiments performed on mouse cortical neurons in culture to test the effect of the amiloride derivatives benzamil and 5-(N-ethyl-N-isopropyl)-amiloride (EIPA) on an acid-induced ASIC current; see FIGS. 11 and 12.

Mouse cortical neurons in culture were monitored electrophysiologically by patch-clamp recording of current at a holding potential of −60 mV. An ASIC current was induced at this holding potential by dropping the extracellular pH from physiological pH (pH 7.4) to pH 6.0, in the presence of different concentrations of benzamil (FIG. 11) or EIPA (FIG. 12). The current traces obtained are presented in the upper part of FIGS. 11 and 12. The amplitude of the measured ASIC current was plotted against the concentration of benzamil or EIPA (μM), as shown in the lower parts of FIGS. 11 and 12 to determine an $IC_{50}$ (concentration at 50% inhibition) of 9.55 μM for benzamil and about 20 μM for EIPA. Therefore, amiloride derivatives inhibit ASIC channel activity and may be used for seizure suppression in subjects prone to seizures and/or having a seizure.

Example 3

Activation of ASICs in CNS Neurons by Repeated pH Drops

Figure 13:
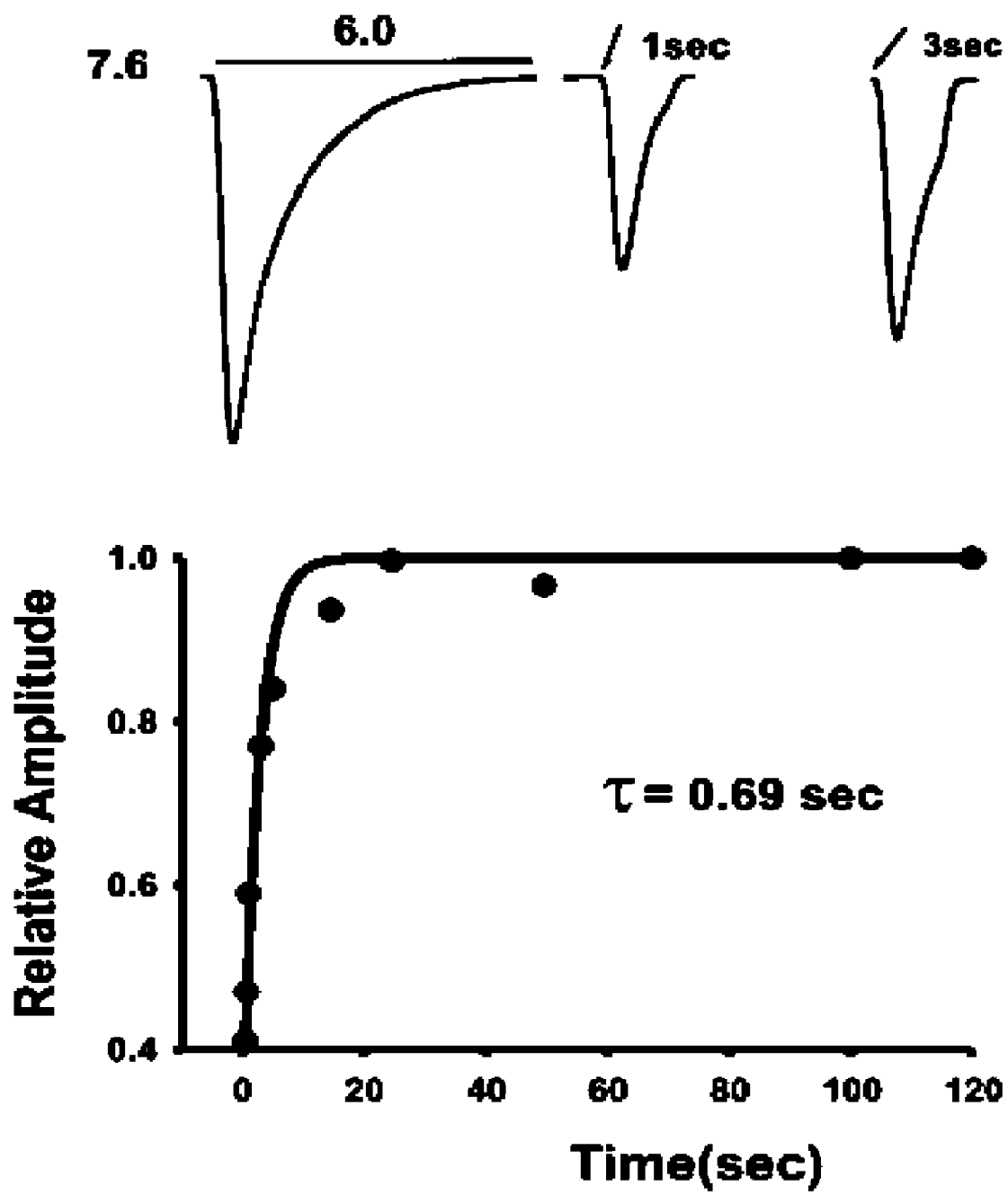
FIG. 13 is a set of graphs presenting exemplary electrophysiological data collected by patch-clamp recording from neurons exposed to a drop to pH 6.0 from pH 7.6, followed by different recovery intervals at pH 7.6 before re-exposure to pH 6.0.

This example describes experiments performed by patch-clamp analysis of mouse cortical neurons in culture to determine the rate of re-sensitization of ASICs at physiological pH after an ASIC desensitization produced by a drop in extracellular pH; see FIG. 13.

Increased neurotransmission as demonstrated by high frequency synchronous firing by populations of neurons is one of the hallmarks of epilepsy. Since synaptic vesicles are highly acidic (pH <5.7), and release of neurotransmitter likely ejects protons into the synaptic cleft, it is expected that pH in the synaptic cleft and extracellular space may undergo fluctuation (up and down) during high frequency synaptic activities. Indeed, in hippocampal slices, others have measured a brief (a few milliseconds) extracellular acidification accompanying EPSPs. Although the measured acid transients in the extracellular space were relatively small (~0.2 pH units), localized changes in the microdomain of the synaptic cleft might be more pronounced. Moreover, a pair of sequential stimuli were reported to reduce pH further, suggesting that acidification might be more prominent when multiple vesicles are released within a short time, for example during seizure activity.

Since ASIC currents may rapidly decay or desensitize with time, it would be interesting to know how fast the ASIC channels can recover from the desensitization process for activation repeatedly by subsequent acid pulses. For this reason, we have performed a study to determine the rate of recovery of the ASICs in cultured mouse cortical neurons (14 days in culture) using whole-cell patch-clamp recording and a fast-perfusion technique. Normal extracellular solutions contained (in mM): 140 NaCl, 5.4 KCl, 25 Hepes, 10 Glucose, 2 CaCl2, 1.0 MgCl2, pH 7.4 using NaOH. For solutions with pH <6.0, MES instead of Hepes was used for more reliable pH buffering. Patch electrodes contained (in mM): 140 CsF, 2.0 MgCl2. 1.0 CaCl2, 10 Hepes, 11 EGTA, 2 MgATP, pH 7.3, using CsOH. A multi-barrel fast perfusion system (SF-77B, Warner Instrument Co.) was employed to achieve a rapid exchange of solutions. ASIC currents were activated by pairs of acid pulses with increasing intervals between the first and the second acid pulse, and a 2 min interval was given for a complete recovery of the channel before the next pair of acid applications. ASIC current was first activated by a 10 sec acid pulse (pH 6.0). Following a complete desensitization of the current at the end of the first acid pulse, a short (1 sec) second acid pulse (pH 6.0) was applied to the neuron at different times following the 1st acid application. The relative amplitude of the second ASIC current versus the first one was then plotted against the time intervals between the end of the first acid pulse and the start of the second pulse. The time constant for the recovery of the ASIC current from its desensitization is then derived by an exponential fit.

FIG. 13 shows that one second following a complete desensitization of the ASIC current, a significant amount of ASIC current can be activated again by another acid application. A detailed analysis yields an average time constant ($\tau$) for the recovery of the current from desensitization of 0.69 sec (n=4). This finding strongly suggests that ASICs can be repeatedly activated by the high frequency acid fluctuation expected to occur in epileptic seizures.

Example 4

Figure 14:
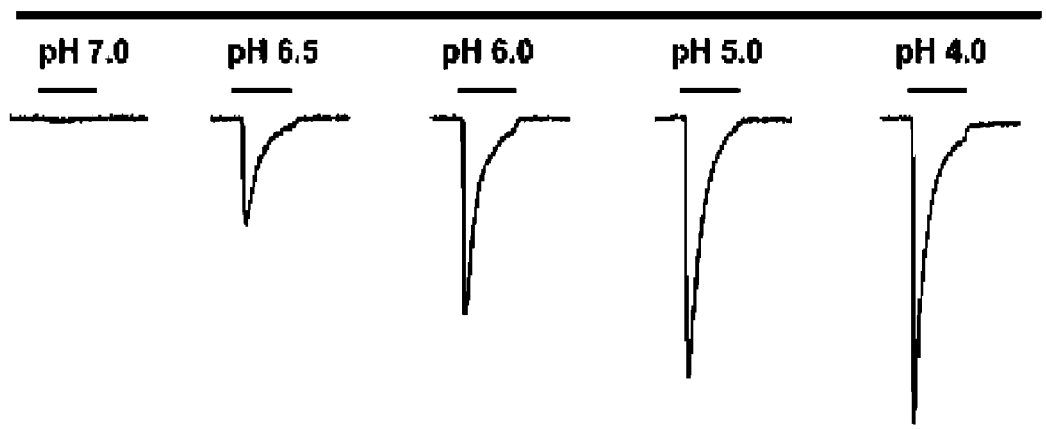
FIG. 14 is a collection of graphs presenting exemplary electrophysiological data collected by patch-clamp recording from neurons exposed to various reduced extracellular pH values at two distinct extracellular $Ca^{2+}$ concentrations.
Figure 14:
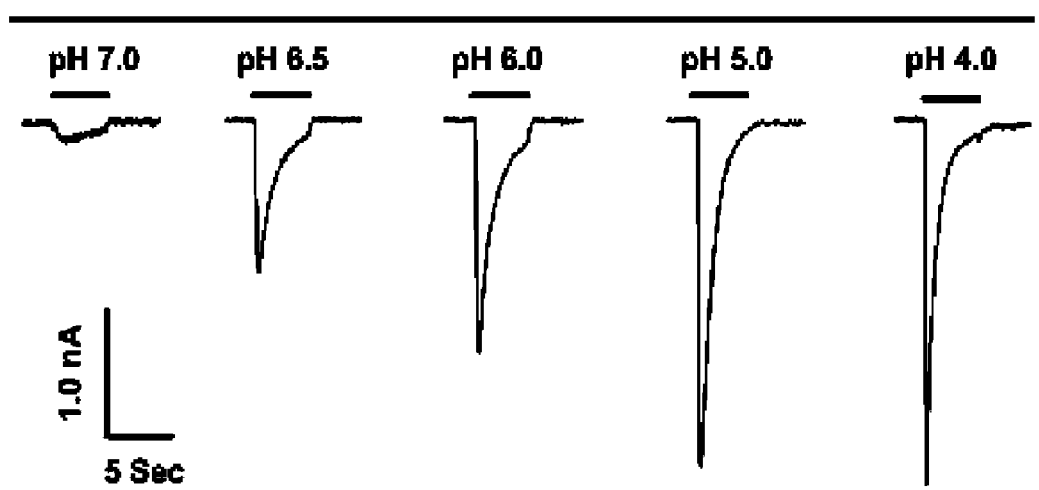
Figure 14:
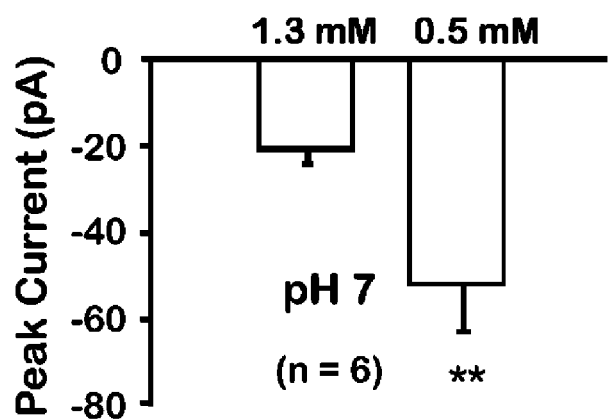

Modulation of ASIC Activities by Biochemical Changes Associated with Epileptic Seizures This example measures the effect of extracellular calcium on ASIC currents in isolated neurons as a function of pH; see FIG. 14.

Repetitive electrical stimulation and intense neuronal activity may produce dramatic decreases (up to 0.5 mM) of extracellular calcium ($[Ca^{2+}]_e$) in the central nervous system. Decreases in $[Ca^{2+}]_e$ have also been evoked by iontophoretic applications of excitatory amino acids. These decreases of $[Ca^{2+}]_e$ may be due largely to excessive release of excitatory neurotransmitters and/or activation of postsynaptic glutamate receptors.

Decreases of $[Ca^{2+}]_e$ may be enhanced dramatically during seizure activity. In pentetrazol-induced seizure, for example, a decrease of $[Ca^{2+}]_e$ by 0.7-1.0 mM has been recorded. It has been noted that the fall of $[Ca^{2+}]_e$ often preceded the onset of seizure events, indicating that the fall of $[Ca^{2+}]_e$ might be responsible for initiating the seizure activities. Decrease of $[Ca^{2+}]_e$ has also been observed by others in chronic models of epilepsy including a kindling model and photically induced seizures. Decreases in $[Ca^{2+}]_e$ are known to increase neuronal excitability. The mechanism by which lowering $[Ca^{2+]}_e$ enhances neuronal excitability is, however, not fully understood, although a host of possibilities has been suggested by others.

Recent studies have shown that the activities of ASIC3 and ASIC1a channels are dramatically modulated by $[Ca^{2+}]_e$. Studies by others demonstrated that ASIC3 channels are normally inhibited by physiological concentrations of $Ca^{2+}$. When $[Ca^{2+}]_e$ is reduced, ASIC activity increases dramatically. Modulation of ASIC1a channels by $[Ca^{2+}]_e$ has also been shown by two recent studies. For example, two negatively charged residues near the entrance of the channel pore, E425 and D432, may be crucial for the $Ca^{2+}$ blockade of the ASIC1a channel. Although the effect of $[Ca^{2+}]_e$ on ASIC3 and ASIC1a have been documented, the effect of $[Ca^{2+}]_e$ on ASICs in native neurons in the CNS has not been studied in detail. Delineating the detailed effects of $[Ca^{2+}]_e$ on the properties of ASICs in native CNS neurons may be important for understanding the precise role of these channels in epileptic seizures where $[Ca^{2+}]_e$ is dramatically altered. A combination of homomeric ASIC1a, heteromeric ASIC1a/ASIC2a and likely ASIC1a/ASIC2b channels have been reported to exist in the neurons of the CNS. Heteromeric channels, in general, may have different electrophysiological and pharmacological properties from the homomeric channels.

We have recorded the effect of lowering $Ca^{2+}$ on the ASIC current in mouse hippocampal neurons. Lowering $[Ca^{2+}]_e$ from 1.3 to 0.5 mM significantly increased the amplitude of the ASIC current (FIG. 14). The increase was more pronounced when the current was activated With a small pH drop (e.g., from 7.4 to 7.0) (FIG. 14, n=6). In addition, an apparent shift of the pH dose-response relationship was observed with reduced $[Ca^{2+}]_e$. For example, in the presence of normal $[Ca^{2+}]_e$ activation of ASIC current required a pH drop to <7.0. However, in the presence of low $[Ca^{2+}]_e$, detectable current could be recorded when the pH was dropped to >7.1. Our studies thus suggest that a leftward shift in the pH dose-response relationship is likely involved in the modulation of the ASICs by lowering $[Ca^{2+}]_e$. This finding may suggest that during seizure activity where a significant decrease of $[Ca^{2+}]_e$ occurs, ASICs can be activated by even a slight pH drop (e.g. by ~0.3 unit). This combination of low $[Ca^{2+}]_e$ and low pH may induce dramatic membrane depolarization thus facilitating the generation of seizure activity.

In addition to decreased $[Ca^{2+}]_e$, a significant drop in the glucose concentration may be associated with epilepsy, particularly in status epilepticus. Our previous report that decreases in extracellular glucose concentration significantly enhance the activity of ASICs further suggests that activation of ASICs plays an important role in the pathophysiology of epilepsy.

Example 5

Effects of Antiepileptic Agents on ASICS

This example describes the effects of three antiepileptic drugs, ethosuximide, felbamate, and lamotrigine, on ASIC currents in isolated neurons; see FIGS. 15A-15C and 16.

Current frontline antiepileptic drugs fall into several cellular mechanistic categories. Drugs effective in control of partial and generalized tonic-clonic seizures are use and voltage-dependent blockers of $Na^+$ channels. Examples include phenytoin, carbamazepine, valproic acid, and lamotrigine. These agents selectively dampen pathologic activation of $Na^+$-channels, without affecting normal $Na^+$-channel function. Drugs effective in control of generalized absence seizures likely block low threshold T-type calcium currents. Examples include ethosuximide, trimethadione, and methsuximide. Agents that augment function of $GABA_A$ receptors, e.g., diazepam and clonazepam, have broad-spectrum antiepileptic effects. Although most AEDs fall into these categories, some AEDs may have clinical antiepileptic effects that cannot be easily explained by the above-mentioned mechanisms. As an example, lamotrigine (LTG) has a broad spectrum of clinical effects against various types of epilepsy. It is effective against both partial and generalized seizures, including absence seizures. Furthermore, LTG has also been used for the treatment of bipolar disorder and pain. The primarily documented cellular mechanism of action is $Na^+$-channel blockade, a mechanism shared by many other antiepileptic agents including phenytoin and carbamazepine. Unlike LTG, however, phenytoin and carbamazepine are ineffective against the absence seizure. Therefore, additional mechanism(s) might be involved in the effects of LTG, to account for its broad clinical efficacy.

Figure 15A:
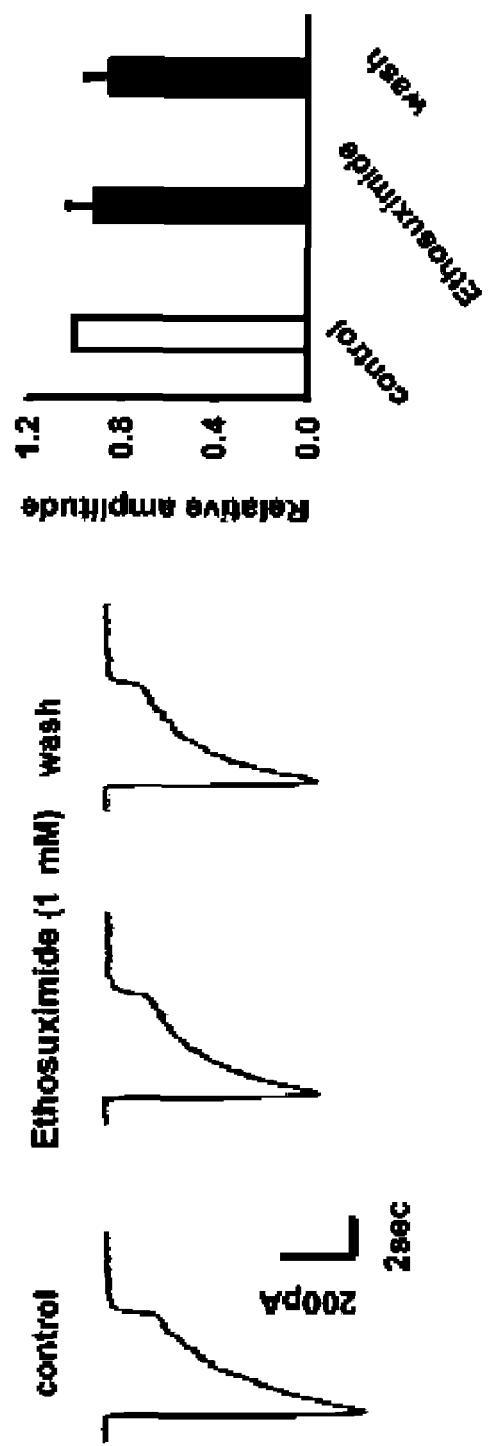
FIGS. 15A-15C are a set of graphs presenting exemplary electrophysiological data collected by patch-cramp recording from neurons exposed to the antiepileptic drugs ethosuximide, lamotrigine, and felbamate.
Figure 15B:
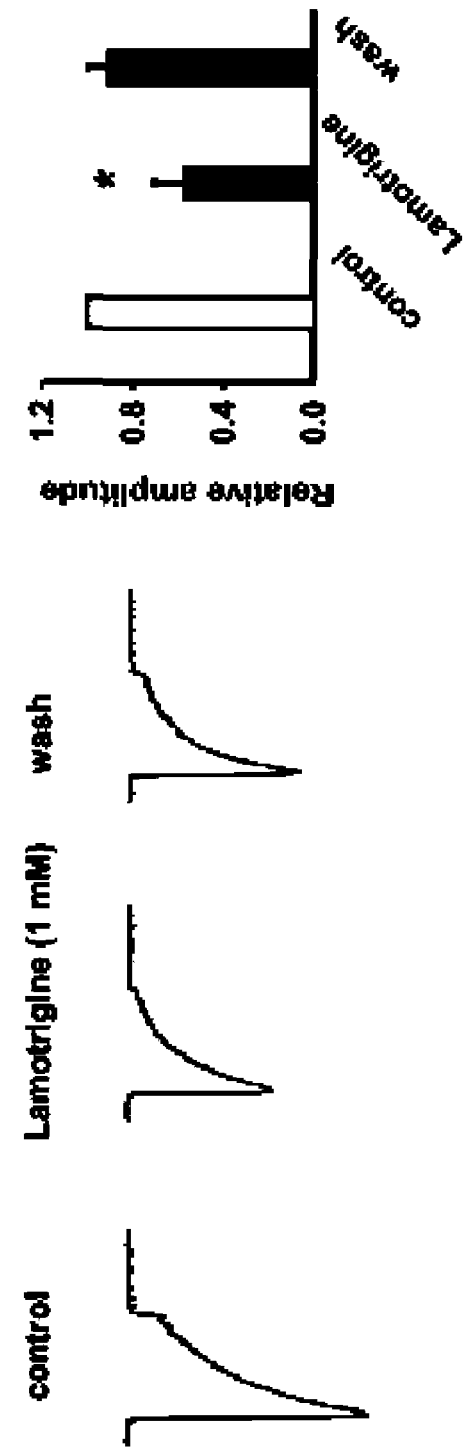
Figure 15C:
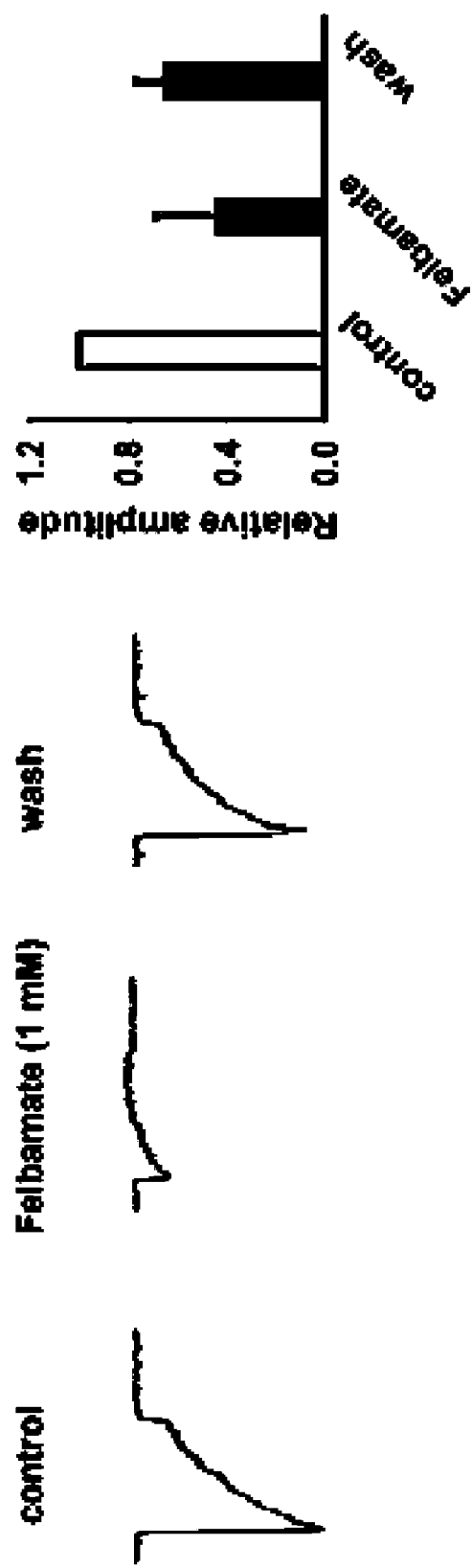
Figure 16:
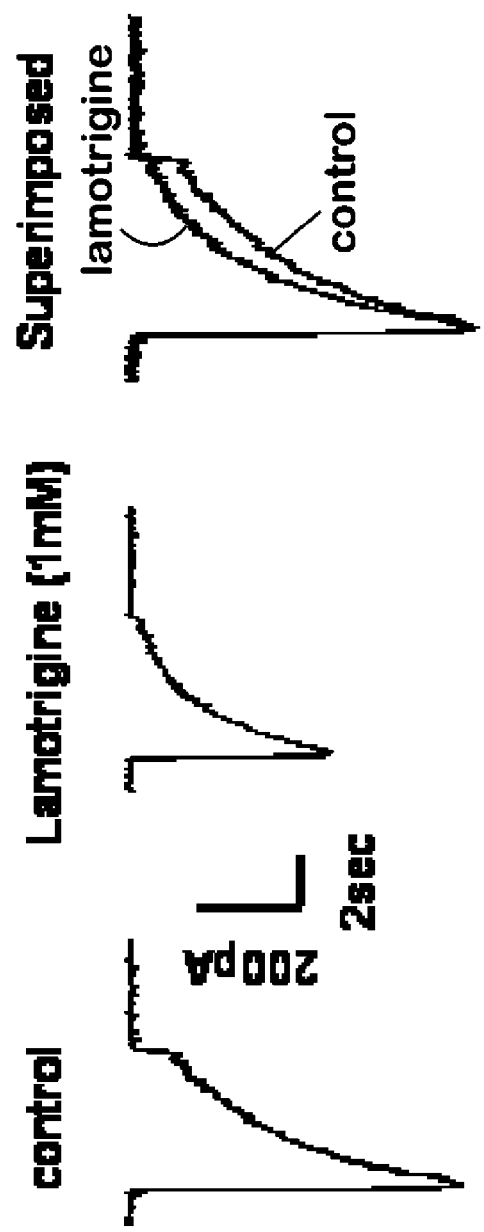
FIG. 16 is a set of graphs presenting exemplary electrophysiological data collected by patch-clamp recording from neurons exposed to the antiepileptic drug lamotrigine.

Activation of ASICs may be involved in increased neuronal excitability and thus seizure generation. Inhibition of ASICs, on the other hand, is expected to be antiepileptic. To test this hypothesis further, we performed a study to examine the effect of currently available antiepileptic agents—particularly those agents for which the mechanism of action is not fully understood—on ASIC currents. We suspected that some of the current antiepileptic agents may, in fact, exert their antiepileptic effect partially through their inhibition of an ASIC current. Three commonly used antiepileptic agents were tested on an ASIC current activated by a pH drop from 7.4 to 6.0. As shown in FIG. 15A, bath application of ethosuximide (1 mM) for 5 min did not affect the amplitude of the ASIC current (n=3). Perfusion of lamotrigine (1 mM), however, inhibited the current by 43±13% (n=3, p<0.05, FIG. 15B), whereas perfusion of 1 mM felbamate reduced the amplitude of the ASIC current by nearly 60% (n=3. FIG. 15C). In addition to decreasing the amplitude of the ASIC current, lamotrigine also enhances the desensitization of the current (FIG. 16). Together, these data suggest that inhibition of the ASIC current may be a mechanism underlying the antiepileptic effect of some antiepileptic drugs.

Example 6

Additional Background

This example provides additional background on ASICs, seizure-induced cell death, and brain acidosis. Citations identifying scientific publications that support statements in Example 6 and elsewhere in the present teachings have been omitted for the sake of brevity. However, U.S. Provisional Patent Application Ser. No. 60/959,987, which is incorporated herein by reference, includes most or all of the omitted citations in its Appendix.

A. ASICs

ASICs, activated by a drop of the extracellular pH ($pH_o$) or by an increase of proton concentration, belong to the amiloride-sensitive epithelial $Na^+$-channel/degenerin superfamily. Members of this family of ion channels may contain two transmembrane spanning regions flanked by a large extracellular loop and short intracellular N— and C-termini. Four genes (ASIC1-ASIC4) encoding six different ASIC members have been cloned to date. ASIC1a (also named ASIC or BNaC2) may be enriched in primary sensory neurons and in most brain regions. ASIC1a channels are reported to be activated by moderate decreases of $pH_o$; the pH for half-maximal activation ($pH_{0.5}$) is ~6.2. In addition to being selective for $Na^+$, homomeric ASIC1a channels may be permeable to $Ca^{2+}$ ions. ASIC1β (or ASIC1b), a splice variant of ASIC1a, has been reported to be expressed only in sensory neurons. When expressed in heterologous systems, ASIC1β apparently forms homomeric channels with a $pH_{0.5}$ of ~5.9. Different from ASIC1a which is $Ca^{2+}$-permeable, ASIC1β is reported to have little $Ca^{2+}$ permeability. Similar to the ASIC1 gene, the ASIC2 gene may be alternatively spliced to code for two variants: ASIC2a and 2b. ASIC2a (also named MDEG, or BNaC1) apparently has a widespread distribution in both peripheral sensory and central neurons. Homomeric ASIC2a channels are reported to have a relatively low sensitivity to $H^+$ with a $pH_{0.5}$ of 4.4, ASIC2b subunits (or MDEG2) apparently are expressed in both peripheral sensory and central neurons. They may not form functional proton-gated channels by themselves, but may associate with other ASIC subunits (e.g., ASIC3) to form heteromultimeric channels. ASIC3 (also named DRASIC) may be expressed predominantly in neurons of dorsal root ganglia. Homomeric ASIC3 is thought to respond to pH drops biphasically with a fast desensitizing current followed by a sustained component. Recently cloned ASIC4 apparently shows high levels of expression in the pituitary gland. However, ASIC4 may not form functional acid-sensing channels alone.

Like other ligand-gated ion channels, ASICs are believed to assemble from homomultimeric or heteromultimeric subunits. The exact subunit combination of ASICs in native neurons, however, is not clear. In the past five years, the electrophysiological properties and pharmacological profiles of recombinant homomeric and heteromeric ASICs in heterologous expression systems have been investigated extensively. These studies have provided information for elucidating the subunit composition of ASICs in native neurons, since different homomeric and heteromeric ASICs have distinct pH sensitivity, ion selectivity, and channel kinetics. The recent findings that tarantula toxin PcTX1 specifically blocks homomeric ASIC1a channels, while sea anemone peptide APETx2 specifically blocks the ASIC3 channels, have provided additional means by which one can investigate the subunit composition of native ASICs. More significant findings related to the subunit composition and functions of ASICs in the brain have been made by gene knockout approaches, combined with electrophysiological recordings and behavioral testing.

The detailed role that ASICs can play is still under active investigation. In peripheral sensory neurons, ASICs have been implicated in mechanosensation and perception of pain during tissue acidosis, particularly in the ischemic myocardium where ASICs likely transduce anginal pain. Recent studies also suggested that activation of ASICS is involved in taste transduction, and maintenance of retinal integrity. The presence of ASICs in the brain, which lacks nociceptors, suggests that these channels in the CNS have functions beyond nociception. Indeed, recent studies have indicated that ASIC1a is involved in synaptic plasticity, learning/memory, and fear conditioning. Our own recent studies demonstrated that activation of $Ca^{2+}$-permeable ASIC1a is also responsible for glutamate-independent, acidosis mediated, ischemic brain injury, disclosing a novel therapeutic target for stroke patients.

Since acidosis is also a common feature of epileptic seizures, particularly during status epilepticus, and since intracellular calcium accumulation is a component of the cytotoxicity of seizure-induced brain injury, activation of ASICs and subsequent membrane depolarization and intracellular $Ca^{2+}$ accumulation may be involved in the neuropathology of epilepsy. Data presented in Example 1 strongly supports this hypothesis.

B. Seizure-induced Cell Death

Human temporal lobe epilepsy may be associated with hippocampal sclerosis in which dentate hilus, CA3, and CA1 neurons are lost, and may be accompanied by mossy fiber sprouting. Similar neuropathological findings have been reported in in vivo experimental models of epilepsy such as kainic acid-lesioned rat hippocampus, in which CA3 neurons and their synapses on to CA1 pyramidal cells are susceptible to cell death. Whether cell loss, synaptic reorganization, or a combination of these factors causes the epileptic condition remains controversial.

More severe brain injury in epilepsy patients may be caused by status epilepticus (SE). In humans, SF may be consistently associated with widespread neuronal necrosis in the hippocampus and other brain regions. In animal models, convulsive SE also may cause extensive neuronal necrosis. Nonconvulsive SE in adult animals also may lead to widespread neuronal injury in vulnerable regions, although lesions may develop more slowly than they would in the presence of convulsive seizures. In SE, glutamate, aspartate, and acetylcholine may play major roles as excitatory neurotransmitters, and GABA may be the dominant inhibitory neurotransmitter. Major increases in cerebral blood flow (CBF) may protect the brain in early SE, but CBF may fall in late SE as blood pressure falls. At the same time, large increases in the cerebral metabolic rate for glucose and oxygen may continue throughout SE. Adenosine triphosphate (ATP) depletion and lactate accumulation may be associated with hypermetabolic neuronal necrosis. Excitotoxic mechanisms mediated by both N-methyl-D-aspartate (NMDA) and non-NMDA glutamate receptors may open ionic channels permeable to calcium and may play a major role in neuronal injury from SE. Hypoxia, systemic lactic acidosis, $CO_2$ narcosis, hypoglycemia, and alteration in ion homeostasis may be common and potentially serious complications of SE.

C. Brain Acidosis

Normal brain may depend on the complete oxidation of glucose, with the end product of $CO_2$ and $H_2O$ for essentially all its energy requirements. During pathological conditions including hypoxia/ischemia, neurotrauma, and epileptic seizure, increased anaerobic glycolysis due to a reduced oxygen supply (particularly for ischemic patients) and/or increased oxygen demand (particularly for seizure patients due to enhanced neuronal excitation) may lead to lactic acid accumulation. Accumulation of lactic acid generally causes a decrease in pH. Extracellular pH typically falls to 6.5 during ischemia. Though riot as severe, a significant drop of brain pH (up to ~0.3 unit) has been reported during intense neuronal excitation or seizure activity. It is also expected that, in the local region of the synaptic cleft, a more severe pH drop may occur. In brain regions such as the adult spinal cord and optic nerve, intense neuronal activity induced by electrical stimulation may induce a predominant extracellular acidification ($pH_o$). In some regions such as cerebellum cortex, and CA1 and CA3 regions of the hippocampus, however, neuronal activity may be accompanied by an initial extracellular alkalinization, followed by acidification.

Changes in $pH_o$ may modulate the activity of a variety of membrane receptors and ion channels. In general, decreased $pH_o$ in thought to inhibit while increased $pH_o$ is thought to potentiate the activities of the majority of voltage-gated and ligand-gated ion channels. For example, NMDA receptor-gated channels may be strongly inhibited by decreases in $pH_o$.

In contrast to its inhibition of membrane receptors and ion channels, an increase in neuronal excitation by acid, as demonstrated by membrane depolarization and repetitive firing of action potentials, has also been demonstrated, though the exact mechanism is unclear.

Example 7

Selected Embodiments

This example describes selected embodiments of the present teachings, presented as a series of indexed paragraphs.

1. A method of screening for anti-seizure drugs, comprising: (A) testing a library of chemical compounds on biological cells for their ability to inhibit a response of the biological cells to a reduced extracellular pH; (B) selecting one or more of the chemical compounds based on results of the step of testing; and (C) assaying at least one drug candidate for an ability to inhibit seizure-like electrical activity and/or seizures, the at least one drug candidate being based on the one or more chemical compounds selected.

2. The method of paragraph 1, and wherein the step of testing includes a step of testing chemical compounds of the library individually.

3. The method of paragraph 1, wherein the step of testing includes a step of testing a mixture of at least two compounds, wherein the step of selecting includes a step of selecting at least the mixture of at least two compounds, and wherein the step of assaying includes a step of assaying each of the at least two compounds individually for an ability to inhibit seizure-like electrical activity and/or seizures.

4. The method of paragraph 1, wherein the step of testing includes a step of exposing the biological cells to a drop in extracellular pH of at least 0.2 pH units.

5. The method of paragraph 1, wherein the step of exposing includes steps of reducing the extracellular pH, increasing the extracellular pH, and then reducing the extracellular pH again.

6. The method of paragraph 1, wherein the step of testing includes a step of optically detecting the response.

7. The method of paragraph 1, wherein the step of testing includes a step of exposing the biological cells to a membrane potential dye, a calcium-sensitive dye, or both.

8. The method of paragraph 1, wherein the step of testing is performed on biological cells engineered to express an acid sensing ion channel.

9. The method of paragraph 1, wherein the step of assaying includes a step of assaying at least one drug candidate that has the same chemical structure as a chemical compound that was selected.

10. The method of paragraph 1, wherein the step of assaying includes a step of assaying at least one drug candidate that is a structural derivative of a chemical compound that was selected.

11. The method of paragraph 1, wherein the step of assaying includes a step of detecting one or more results for the at least one drug candidate with a patch-clamp technique.

12. A method of screening for anti-seizure drugs, comprising: (A) testing a library of chemical compounds for their ability to inhibit at least one acid sensing ion channel (ASIC); (B) selecting one or more of the chemical compounds that inhibit the at least one ASIC; and (C) assaying at least one drug candidate for an ability to inhibit seizure-like electrical activity and/or seizures, the at least one drug candidate being based on the one or more chemical compounds selected.

13. The method of paragraph 12, wherein the step of testing is performed, at least in part, on biological cells engineered to express an ASIC protein.

14. The method of paragraph 12, wherein the step of testing is performed with biological cells and includes a step of detecting the biological cells optically.

15. A method of screening for anti-seizure drugs, comprising;
testing a plurality of compositions for an ability to affect a response of biological cells to a reduced extracellular pH and/or to affect an activity of at least one acid sensing ion channel; and
selecting a drug for seizure suppression from one or more drug candidates that were chosen, at least in part, based on results of the step of testing.

16. A method of treating seizures, comprising:
suppressing one or more seizures in a subject prone to seizures and/or having a seizure with an effective amount of PcTX1, a peptide derivative of PcTX1, amiloride, an amiloride derivative, or a combination thereof.

17. The method of paragraph 16, wherein the step of suppressing includes a step of administering the effective amount to a person afflicted with status epilepticus.

18. A method of treating seizures, comprising:
administering, to a subject prone to seizures and/or having a seizure in order to suppress seizure activity, an effective amount of a drug selected, at least in part, based on results of a screen for ASIC inhibitors.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of screening for anti-seizure drugs, comprising:
testing a library of compounds for an ability to inhibit an ion channel activity of at least one acid sensing ion channel (ASIC) at a pH that activates the ASIC;
selecting one or more compounds from the library that have the ability to inhibit in a manner selective or specific for the ASIC relative to most or all ion channels that are not ASICs; and
assaying the one or more compounds for inhibition of seizure-like electrical activity and/or seizures.

2. The method of claim 1, wherein the step of selecting includes a step of selecting one or more compounds each capable of inhibiting acid sensing ion channel 1a (ASIC1a).

3. The method of claim 1, wherein the step of assaying includes a step of assaying at least one analog of at least one of the one or more compounds selected.

4. The method of claim 1, wherein the step of testing includes a step of performing optical assays, and wherein the step of selecting one or more compounds is based on results from the optical assays.

5. The method of claim 1, wherein the step of assaying includes a step of assaying the one or more compounds in a clinical trial.

6. The method of claim 1, wherein the step of assaying includes a step of assaying the one or more compounds on a tissue explant from brain.

7. The method of claim 1, wherein the step of assaying includes a step of using a patch-clamp technique.

8. The method of claim 1, wherein the step of assaying includes a step of administering a peptide analog of PcTX1 or an amiloride analog to a subject.

9. The method of claim 8, wherein the step of administering includes a step of administering an amiloride analog to the subject.

10. The method of claim 8, wherein the step of administering includes a step of administering an amiloride derivative with the structural formula

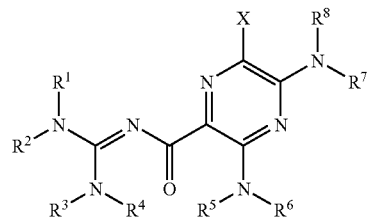

wherein substituent X is a halogen moiety,
wherein each of substituents $R^1$-$R^8$ is independently selected from H, alkyl having 1-12 carbons, arylalkyl having 7-13 carbons, aryl, or heteroaryl,
wherein, if one or more of substituents $R^1$-$R^8$ is alkyl or arylalkyl, an alkyl portion of each aryl or arylalkyl substituent independently and optionally may be further substituted one or more times by halogen, hydroxy, alkoxy having 1-6 carbons, aryl, heteroaryl, amino, alkylamino having 1-6 carbons, dialkylamino having 2-12 carbons, carboxylic acid, or an ester formally derived from carboxylic acid and an alcohol having 1-6 carbons, and
wherein, if one or more of substituents $R^1$-$R^8$ is aryl, arylalkyl, or heteroaryl, an aromatic portion of each aryl, arylalkyl, or heteroaryl substituent independently and optionally may be further substituted one or more times by halogen, alkyl having 1-6 carbons, amino, alkylamino having 1-6 carbons, dialkylamino having 2-12 carbons, carboxylic acid, or an ester formally derived from carboxylic acid and an alcohol having 1-6 carbons.

11. The method of claim 8, wherein the step of administering includes a step of administering parenterally.

12. The method of claim 8, wherein the step of administering includes a step of administering a peptide analog of PcTX1 to the subject.

13. The method of claim 8, further comprising a step of selecting a person with epilepsy, wherein the step of administering is performed on the person with epilepsy.

14. The method of claim 8, wherein the step of administering includes a step of administering while the subject is not having a seizure.

15. The method of claim 1, wherein the step of testing includes a step of testing the library of compounds using biological cells modified to express the at least one acid sensing ion channel (ASIC).

16. The method of claim 15, wherein the step of testing uses biological cells that have been modified by introduction of a nucleic acid encoding acid sensing ion channel 1a (ASIC1a).

17. The method of claim 1, wherein the step of assaying includes a step of assaying the one or more compounds for an ability to inhibit an onset of seizure-like electrical activity and/or seizures.

* * * * *